United States Patent [19]
Kontos

[11] Patent Number: 5,997,555
[45] Date of Patent: Dec. 7, 1999

[54] DEVICE AND METHOD FOR SUTURING BLOOD VESSELS

[75] Inventor: Stavros Kontos, Woodcliff Lake, N.J.

[73] Assignee: X-Site, L.L.C., Totowa, N.J.

[21] Appl. No.: 09/071,272

[22] Filed: May 1, 1998

[51] Int. Cl.[6] .................................................. A61B 17/04
[52] U.S. Cl. ............................................................ 606/148
[58] Field of Search .................................... 606/148, 144, 606/138, 139, 145, 149, 222, 224, 213, 205, 228

[56] References Cited

U.S. PATENT DOCUMENTS

| | | | |
|---|---|---|---|
| 5,292,327 | 3/1994 | Dodd et al. | 606/148 |
| 5,324,298 | 6/1994 | Phillips et al. | 606/148 |
| 5,336,229 | 8/1994 | Noda | 606/144 |
| 5,423,837 | 6/1995 | Mericle et al. | 606/148 |

Primary Examiner—Michael Buiz
Assistant Examiner—Vikki Trinh
Attorney, Agent, or Firm—Kenyon & Kenyon

[57] ABSTRACT

A device for sealing openings in anatomical structures comprises a longitudinal member including a proximal portion having a longitudinal suture channel extending therethrough and a central portion, wherein the suture channel extends through the central portion to a suture opening formed in the central portion distal end and a distal portion coupled to the central portion distal end. A plurality of needle channels extend substantially longitudinally through the distal portion from the distal portion proximal end and, in an initial configuration, each of needle channel incldes a needle with a length of suture forming a suture loop coupled between respective pairs of needles, so that, when the suture loop is pulled in a proximal direction, the length of suture pulls each of the needles to which the length of suture is coupled from the initial position to a deployed position in which proximal ends of each of the needles coupled to the length of suture extend outside the corresponding needle channels.

27 Claims, 30 Drawing Sheets

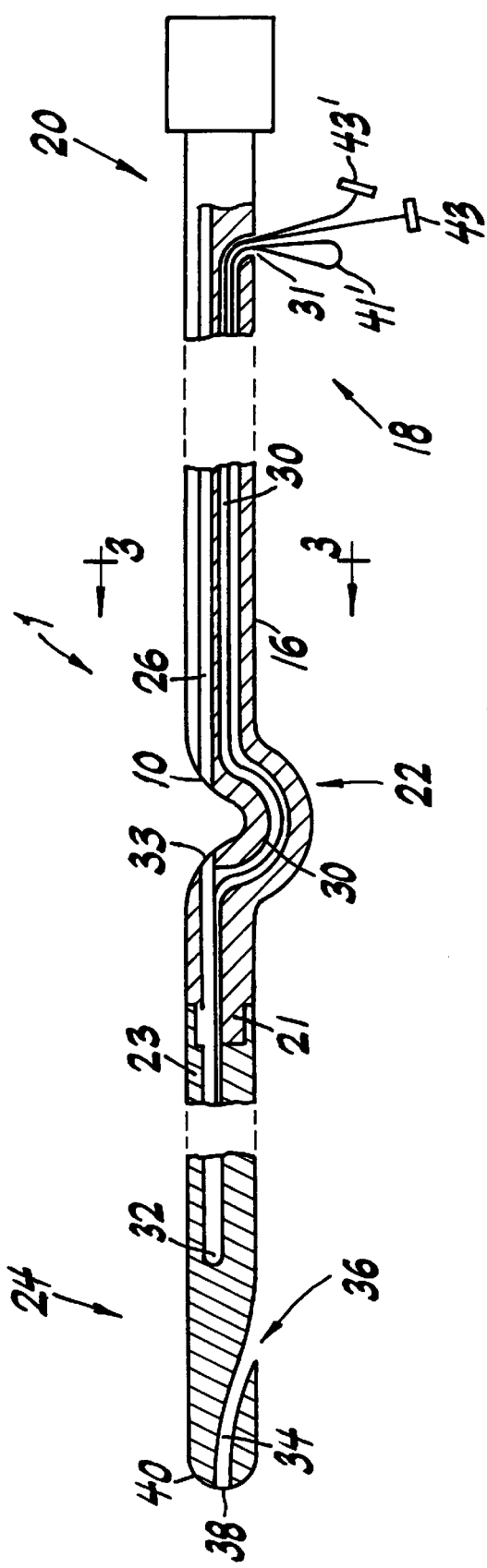
FIG. 1
FIG. 3A
FIG. 3B

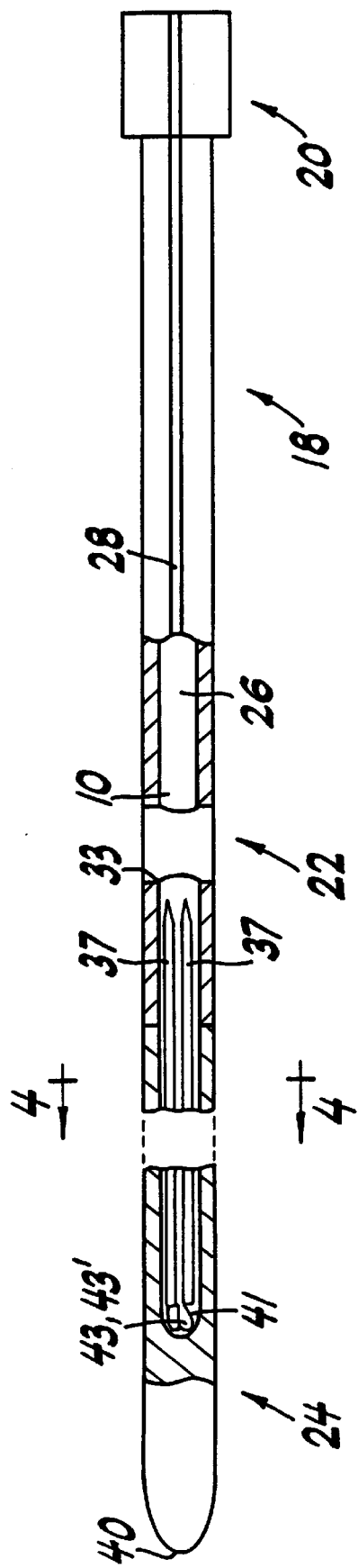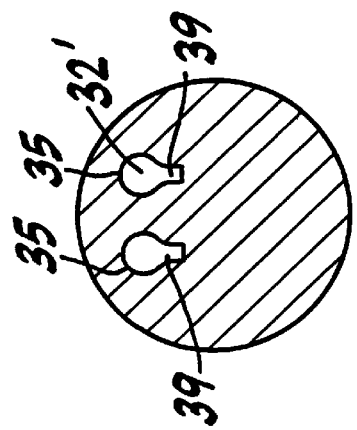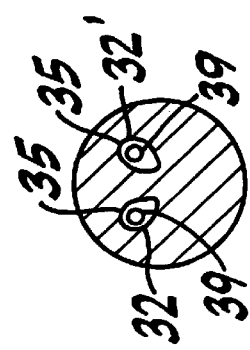
FIG. 2
FIG. 4A
FIG. 4B

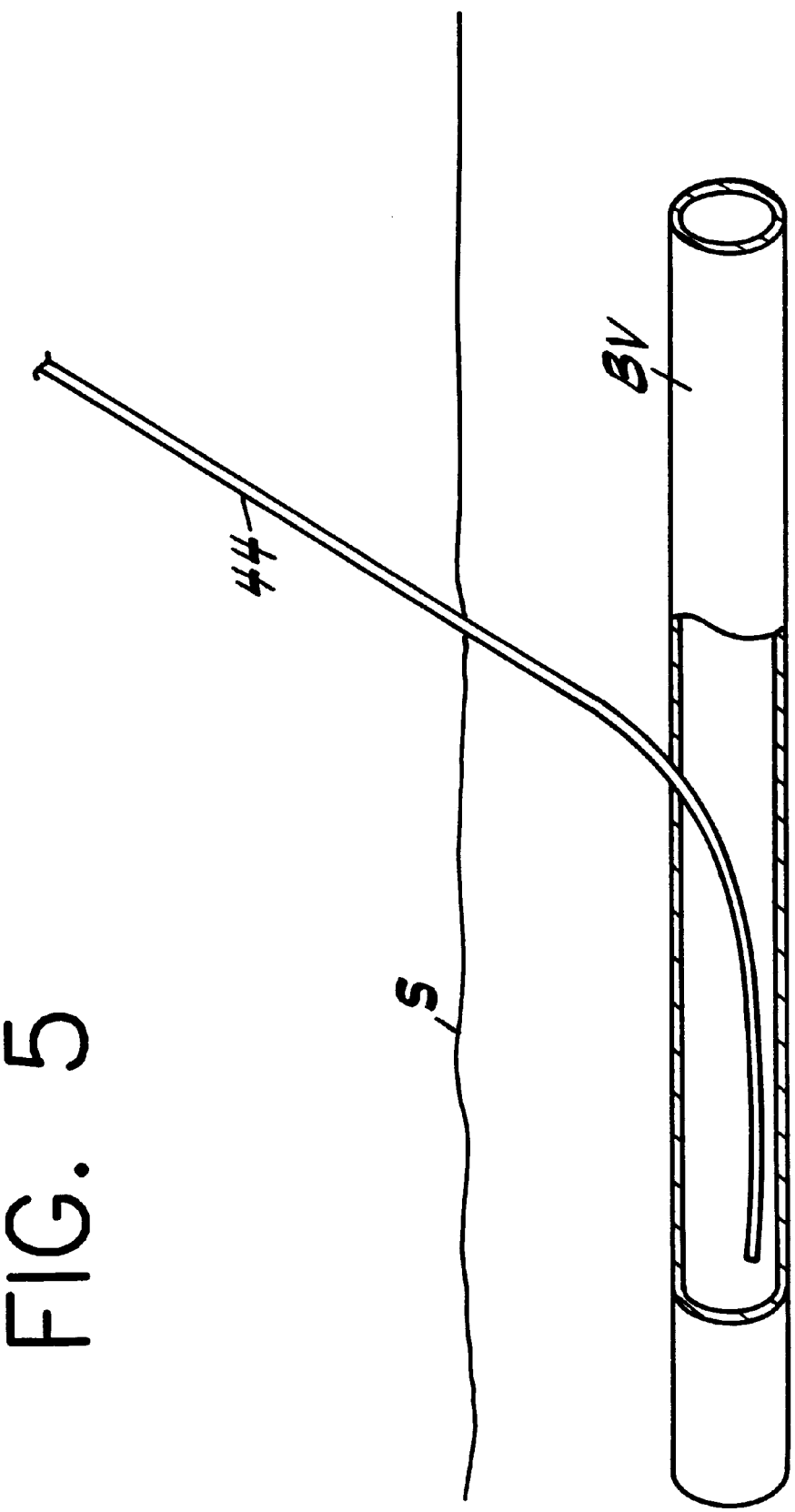

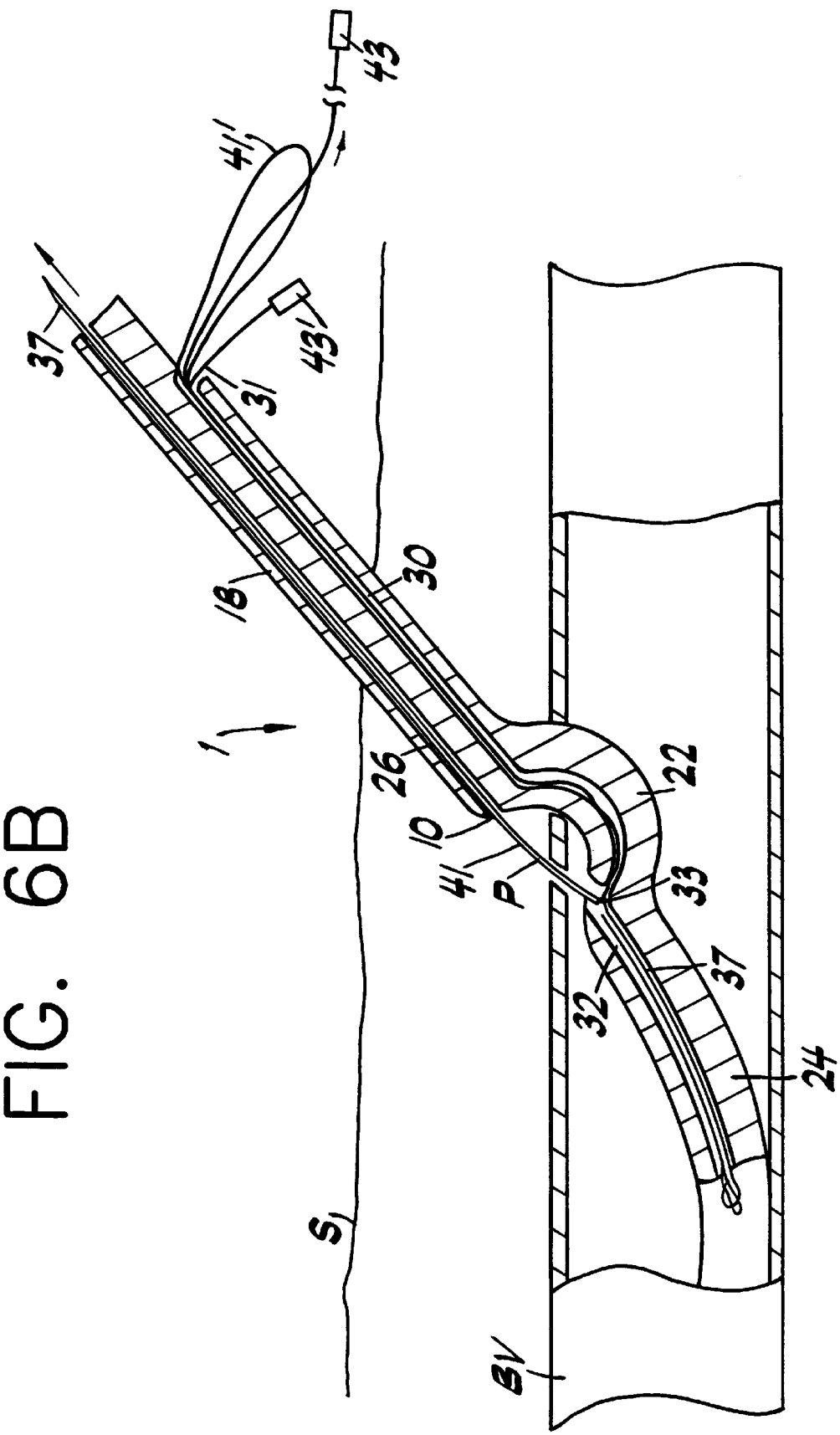

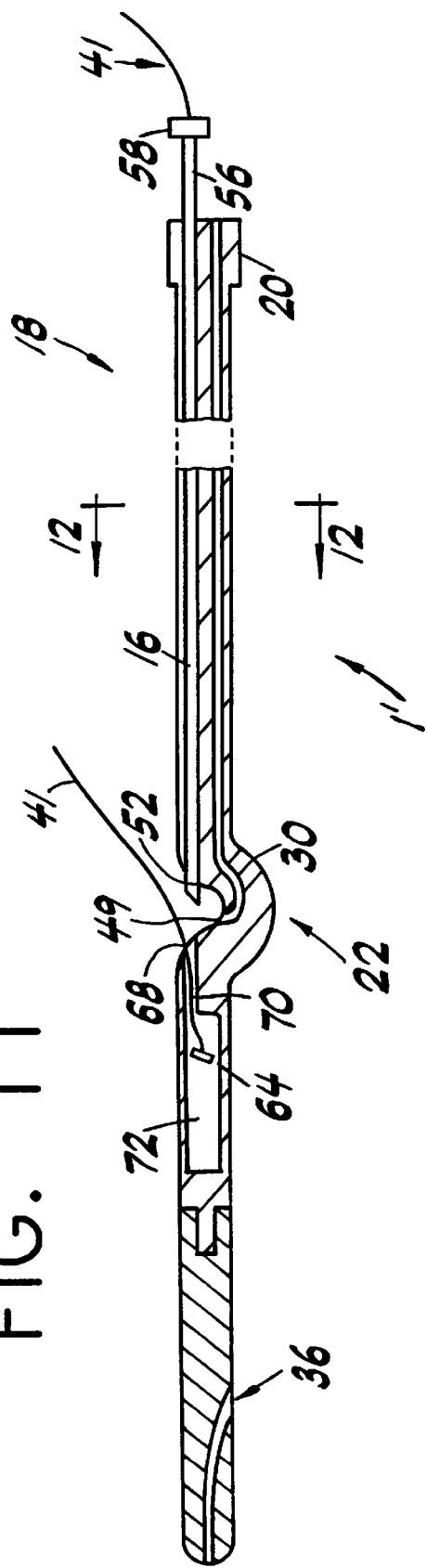

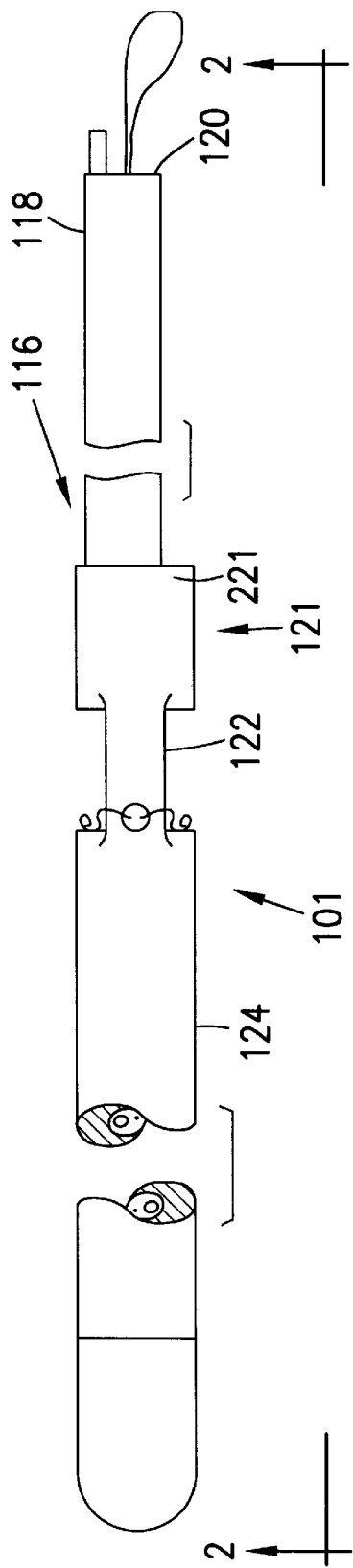
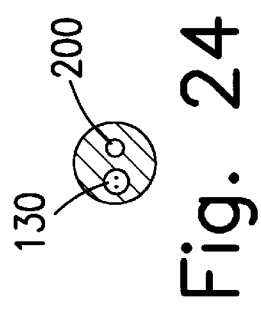
Fig. 22
Fig. 24
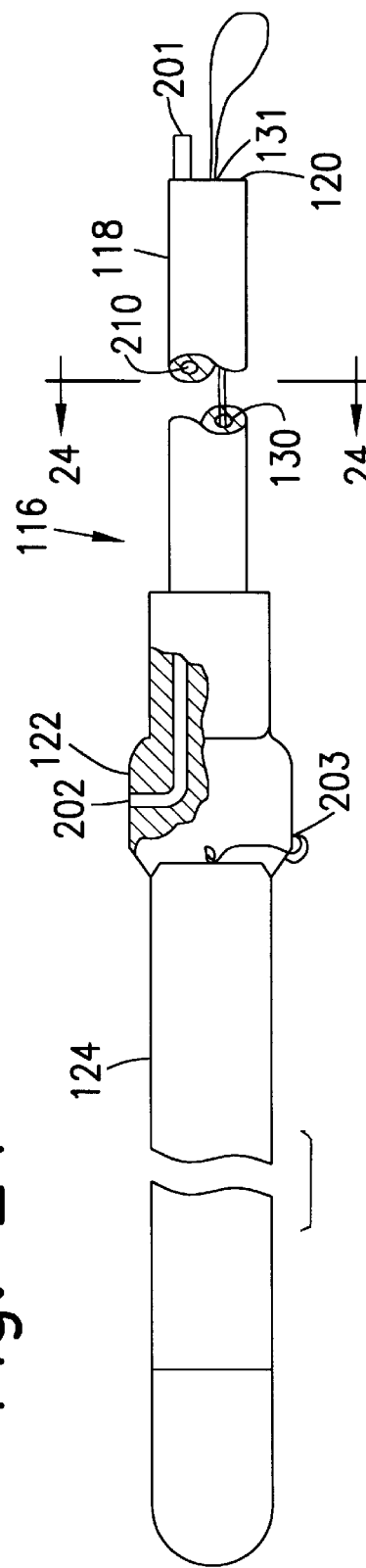
Fig. 23

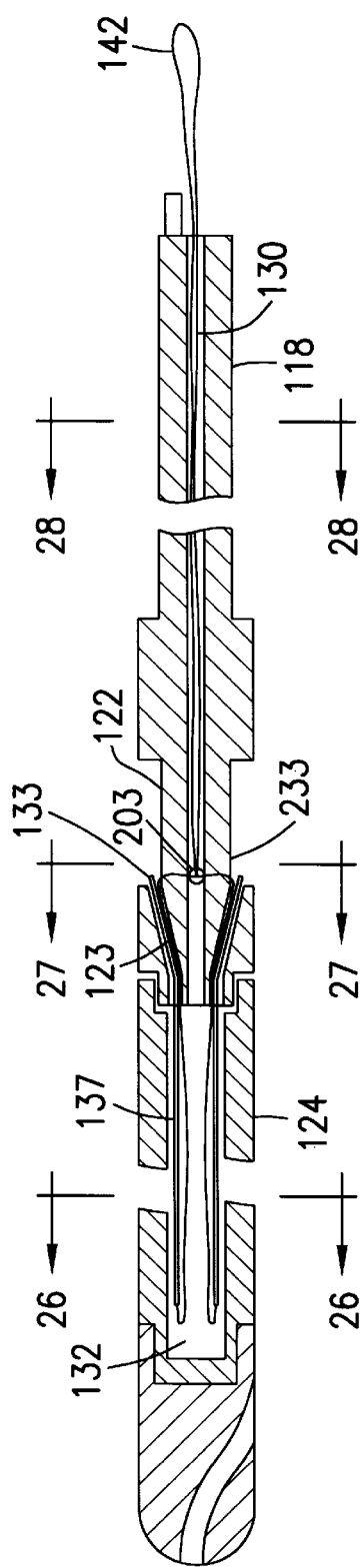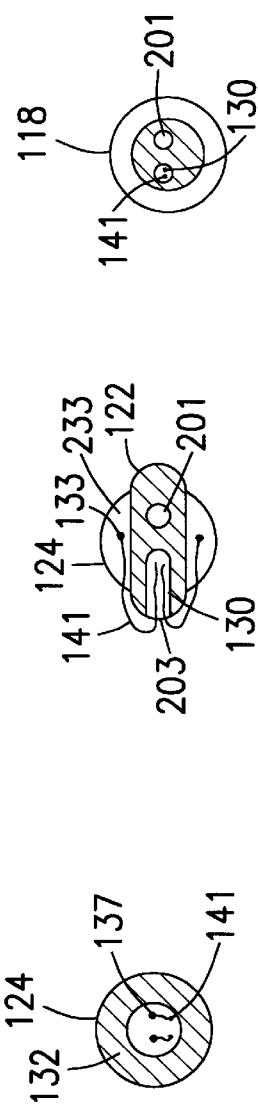
Fig. 25
Fig. 26
Fig. 27
Fig. 28

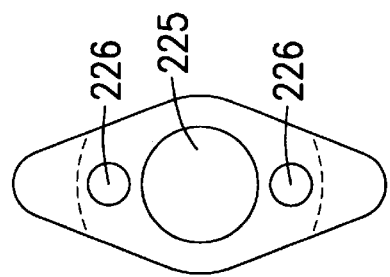
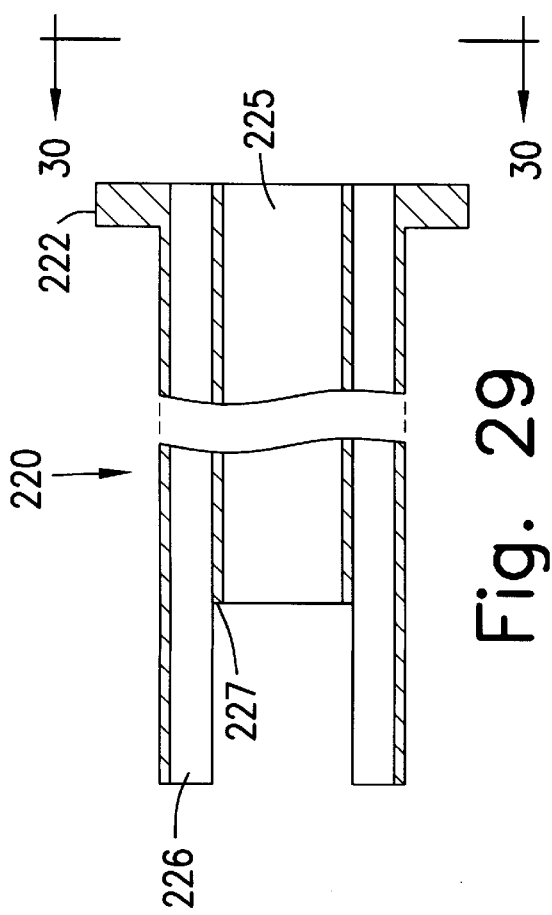
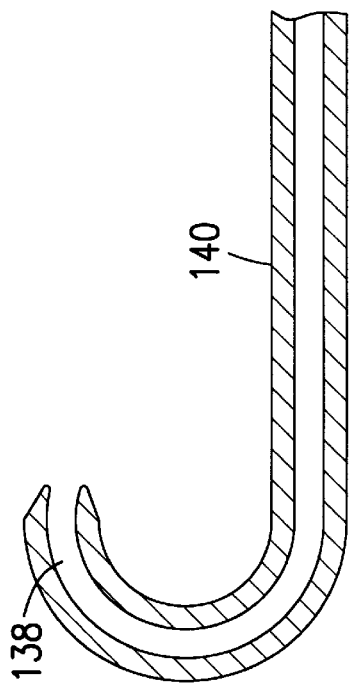

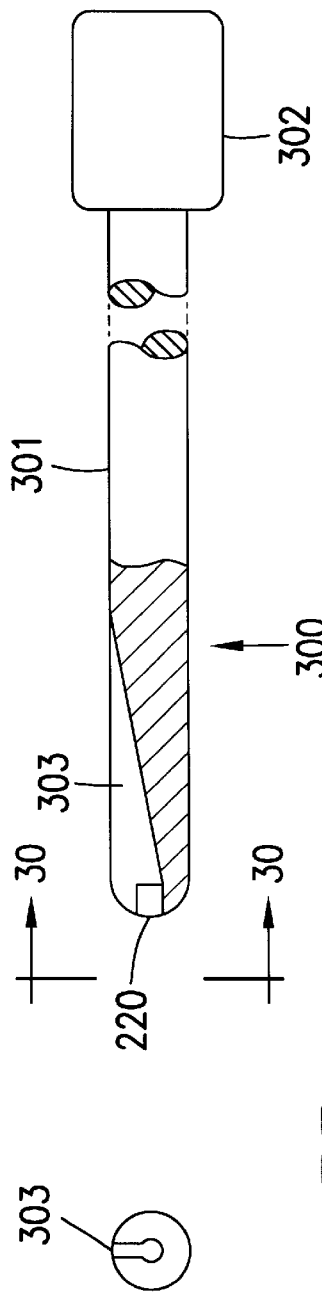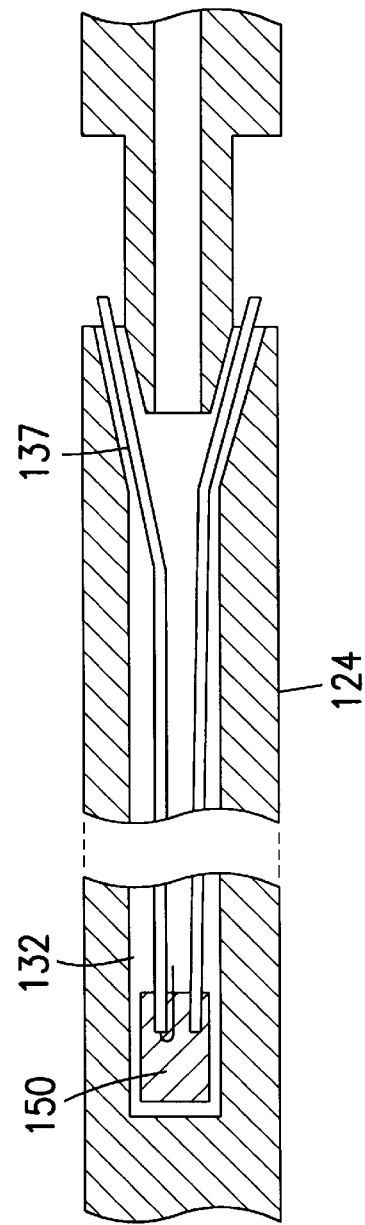

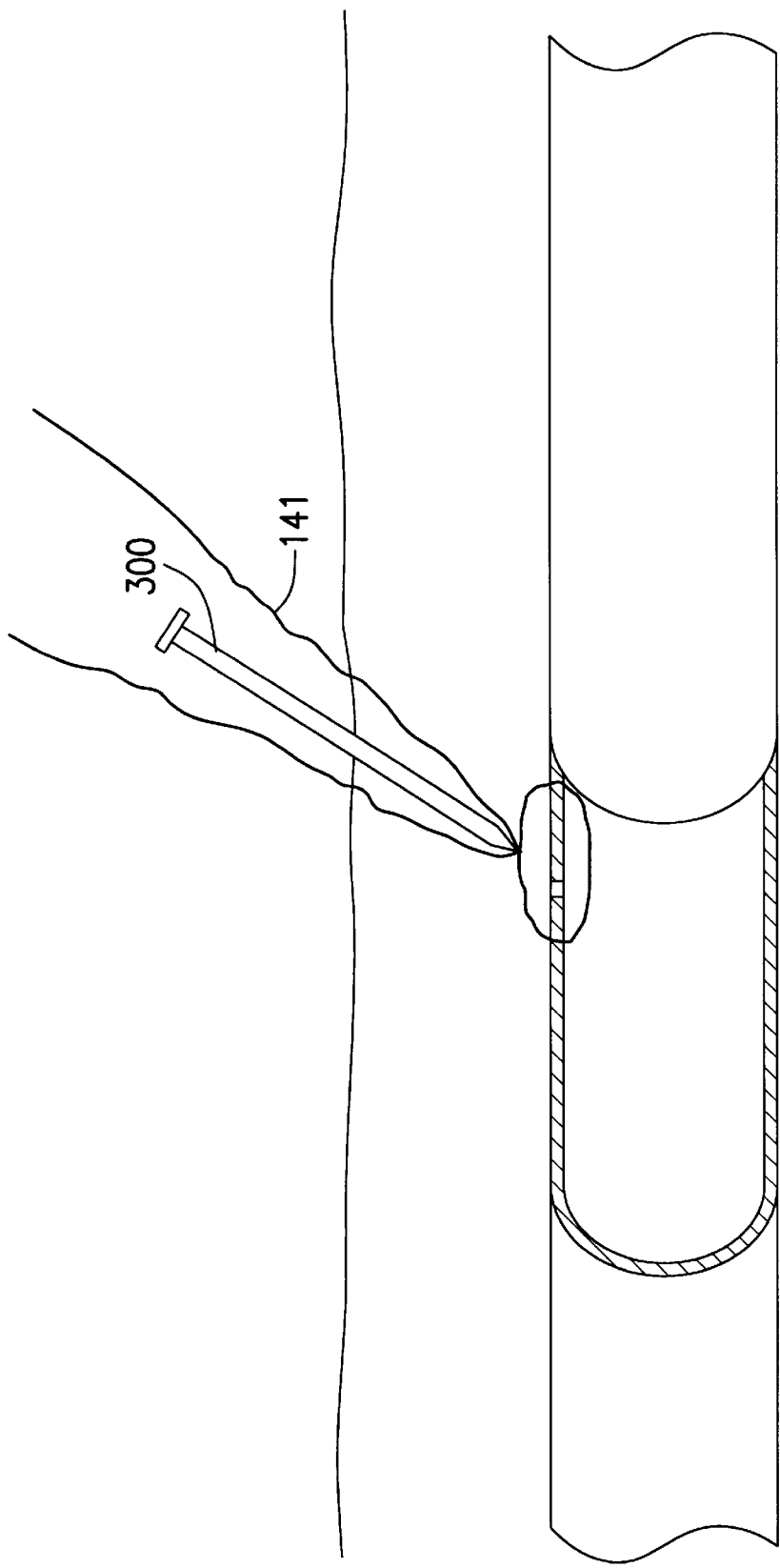

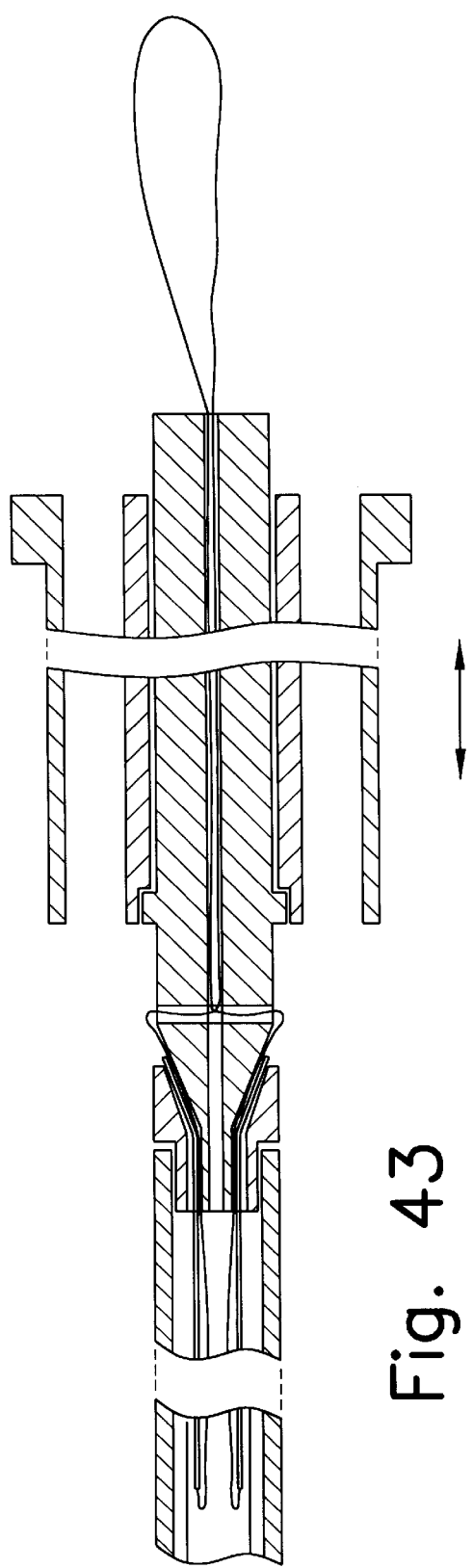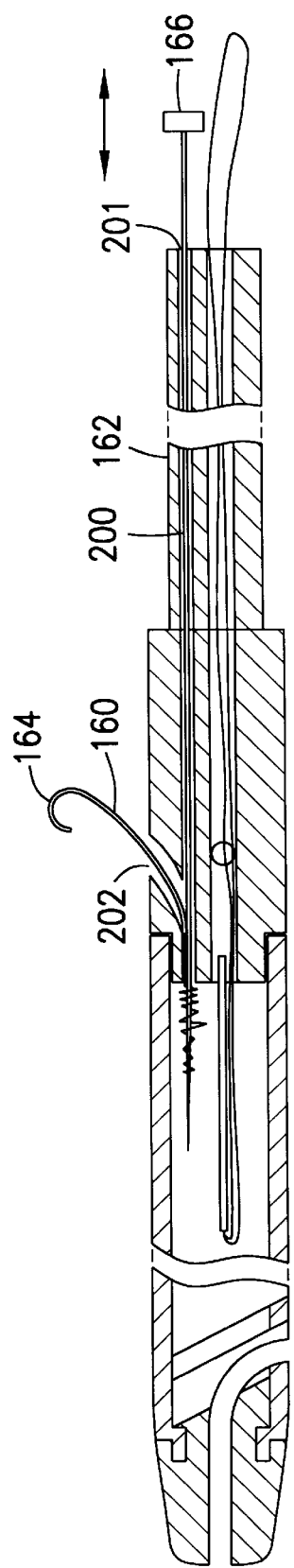

DEVICE AND METHOD FOR SUTURING BLOOD VESSELS

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into an internal structure. Once inside the internal structure, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a device for sealing openings in anatomical structures comprising a longitudinal member including a proximal portion having a longitudinal suture channel extending therethrough and a central portion, wherein the suture channel extends through the central portion to a suture opening formed in the central portion distal end and a distal portion coupled to the central portion distal end. A plurality of needle channels extend substantially longitudinally through the distal portion from the distal portion proximal end and, in an initial configuration, each of needle channel includes a needle with a length of suture forming a suture loop coupled between respective pairs of needles, so that, when the suture loop is pulled in a proximal direction, the length of suture pulls each of the needles to which the length of suture is coupled from the initial position to a deployed position in which proximal ends of each of the needles coupled to the length of suture extend outside the corresponding needle channels.

The present invention is also directed to a method for sealing an opening in an anatomical structure comprising the steps of guiding into the opening a device including a longitudinal member having a proximal portion with a suture channel extending therethrough and a central portion, wherein the suture channel extends through the central portion to a suture opening formed in the distal end of the central portion. A distal portion of the longitudinal member includes a plurality of longitudinal needle channels extending distally therethrough with a plurality of needles each being disposed within a respective one of the plurality of needle channels wherein a length of suture forms at least one suture loop with the suture loop extending through the suture lumen, the suture opening, and a respective one of the plurality of needle channels to suture ends each of which is connected to a distal end of a respective needle. The device is positioned so that the distal portion is received within the anatomical structure and the proximal portion is outside the anatomical structure, so that a portion of a wall of the anatomical structure is received between the proximal and distal portions and the suture loop is drawn proximally to draw the needles coupled to the suture ends through the wall of the anatomical structure until the needles can be grasped and drawn proximally to draw the suture loop distally through the suture lumen into the anatomical structure. The suture ends are then separated from the needles and the suture ends are fastened together to form a knot which is tightened to seal the opening in the length of suture.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 5 shows a partially cross-sectional view of a blood vessel within a body with a guide wire inserted therein;

FIG. 6B shows a partially cross-sectional view of the blood vessel with the device as shown in FIG. 6A wherein a needle has been drawn through the body tissue received in the central gap;

FIG. 11 shows a side view of a cross-section of a suturing device according to a second embodiment of the invention;

FIG. 12 shows a cross-section of a device according to the second embodiment of the invention taken along line 12—12 of FIG. 11;

FIG. 22 shows a side view of a fifth embodiment of the suture device according to the present invention;

FIG. 23 shows a side view of the suture device of FIG. 22, with the device rotated 90° from the position shown in FIG. 22;

FIG. 24 shows a cross-sectional view of the suture device of FIG. 23 taken along the line 24—24;

FIG. 25 shows a side view of the suture device of FIG. 22;

FIG. 26 shows a cross-sectional view of the suture device of FIG. 25 taken along the line 26—26;

FIG. 27 shows a cross-sectional view of the suture device of FIG. 25 taken along the line 27—27;

FIG. 28 shows a cross-sectional view of the suture device of FIG. 25 taken along the line 28—28;

FIG. 29 shows a side view of a needle receiving body according to the present invention;

FIG. 30 shows a cross-sectional view of the needle receiving body of FIG. 29 taken along line 30—30;

FIG. 31 shows a side view of a distal end of another embodiment of the suture device according to the present invention;

FIG. 32 shows a side view of a knot pusher according to the present invention;

FIG. 33 shows a cross-sectional view of the knot pusher of FIG. 32 taken along line 33—33;

FIG. 41 shows a perspective view of a knot pusher according to the present invention pushing a knotted length of suture;

FIG. 42 shows a side view of another embodiment of the suture device according to the present invention;

FIG. 43 shows a side view of a suture device according to the present invention including a needle receiving body according to the present invention.

FIG. 44 shows a side view of an embodiment of a suture device according to the present invention having a retractable anchor.

DETAILED DESCRIPTION OF THE INVENTION

Figure 6A:
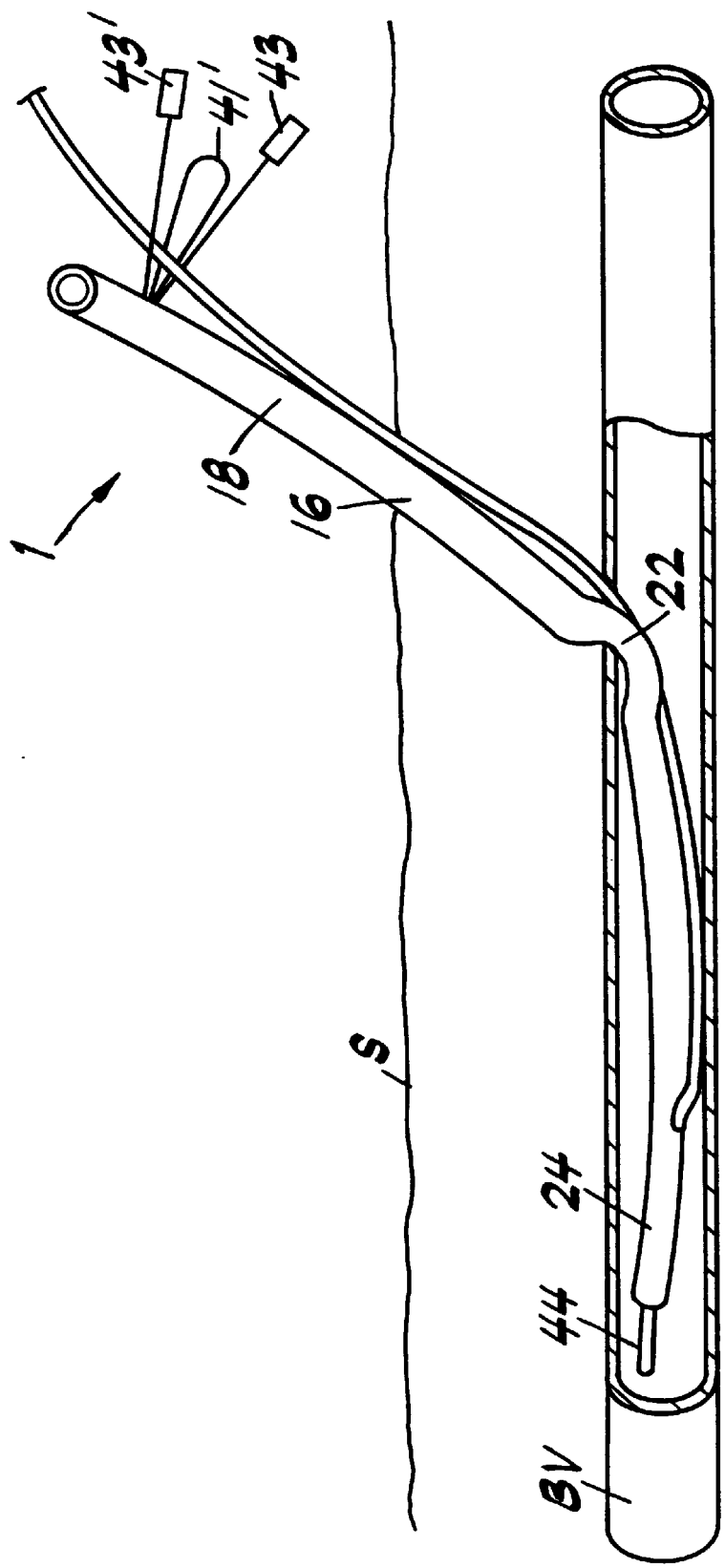
FIG. 6A shows a partially cross-sectional view of the blood vessel with a device according to the first embodiment of the present invention received on the guide wire in a first desired position.

Referring now to the drawings, in which like reference numerals identify similar or identical elements, FIGS. 1–8 show a device 1 according to a first embodiment of the invention for suturing punctures in blood vessels, internal organs and the like. The device 1 includes flexible tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a diameter of from 0.100" to 0.600". The flexible tube 16 is preferably constructed of a thermoplastic such as polyurethane, polyethylene, or the like, in two or three parts bonded together. The various parts of the flexible tube 16 may preferably be either extruded or molded. Those skilled in the art will recognize that it will be more economical to extrude the parts including one or two lumens, while the more complex, and curved sections of the flexible tube 16 may be molded. The length of the flexible tube may be selected to fit the requirements of a particular situation and is preferably between 1" and 16" in length.

The flexible tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the flexible tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37 is not accidentally drawn out of the needle retention bore 32' when the first 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 and second portions 39, each shaped to receive a suture 41 and pull cord 43 or 43'. The first portions 35 are shaped to correspond to the cross-section of the needles 37 which in the preferred embodiment is substantially circular. The second portions 39, which are of reduced size so that the needles 37 are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 extended through the flash back lumen 30 so that, when the loop 41' of the suture 41 is extended proximally, the needles 37 are urged proximally through the needle retention bores 32 and 32'.

As the device 1 according to the first embodiment includes a single pair of needles, this device should preferably be used to close punctures of 9.0 French size and smaller (each French size representing 0.13" in diameter). The flexible tube 16 will, therefore, preferably be 6.0 or 8.0 French size. As described below in reference to further embodiments of the invention, devices employing two or more pairs of needles 37 may be employed to close punctures larger than 9.0 French size. Each of the needles 37 may preferably be constructed of stainless steel, be between 2" and 8" in length and have a diameter between 0.010" and 0.030".

When the device 1 is in an operative configuration, the suture 41 extends between the distal ends of two needles 37 received in the needle retention bores 32 and 32'. In the first embodiment of the invention, optional pull cords 43, 43' extend from the distal end of each of the needles 37 through the second portions 39 of the needle retention bores 32 and 32', via the flash back lumen 30, to the opening 31. However, the suture 41 may, alternatively, extend from the distal ends of the needles 37 through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the flexible tube 16 bends so that the device 1 is received within, and extends in the direction of the blood vessel without straining the vessel. In this position, the openings 33 and 33' are on the distal side of the puncture facing the opening 10 which is located on the proximal side of the puncture.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 will extend through the needle withdrawal lumen 26, the needles 37 will preferably be at least 4" in length.

Figure 7:
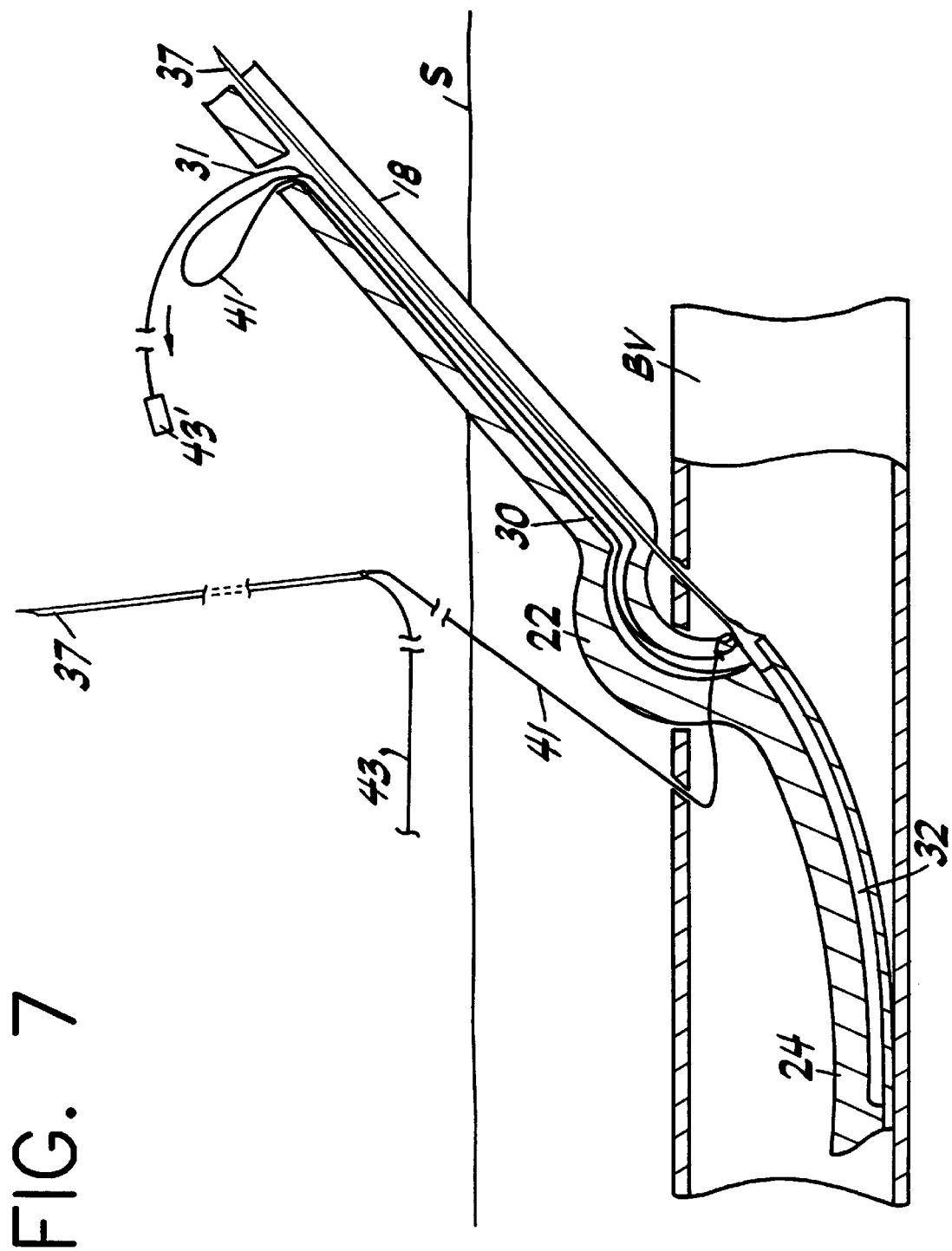
FIG. 7 shows a partially cross-sectional view of the blood vessel with a device according to the first embodiment of the present invention in a second desired position.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening 10 and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 8:
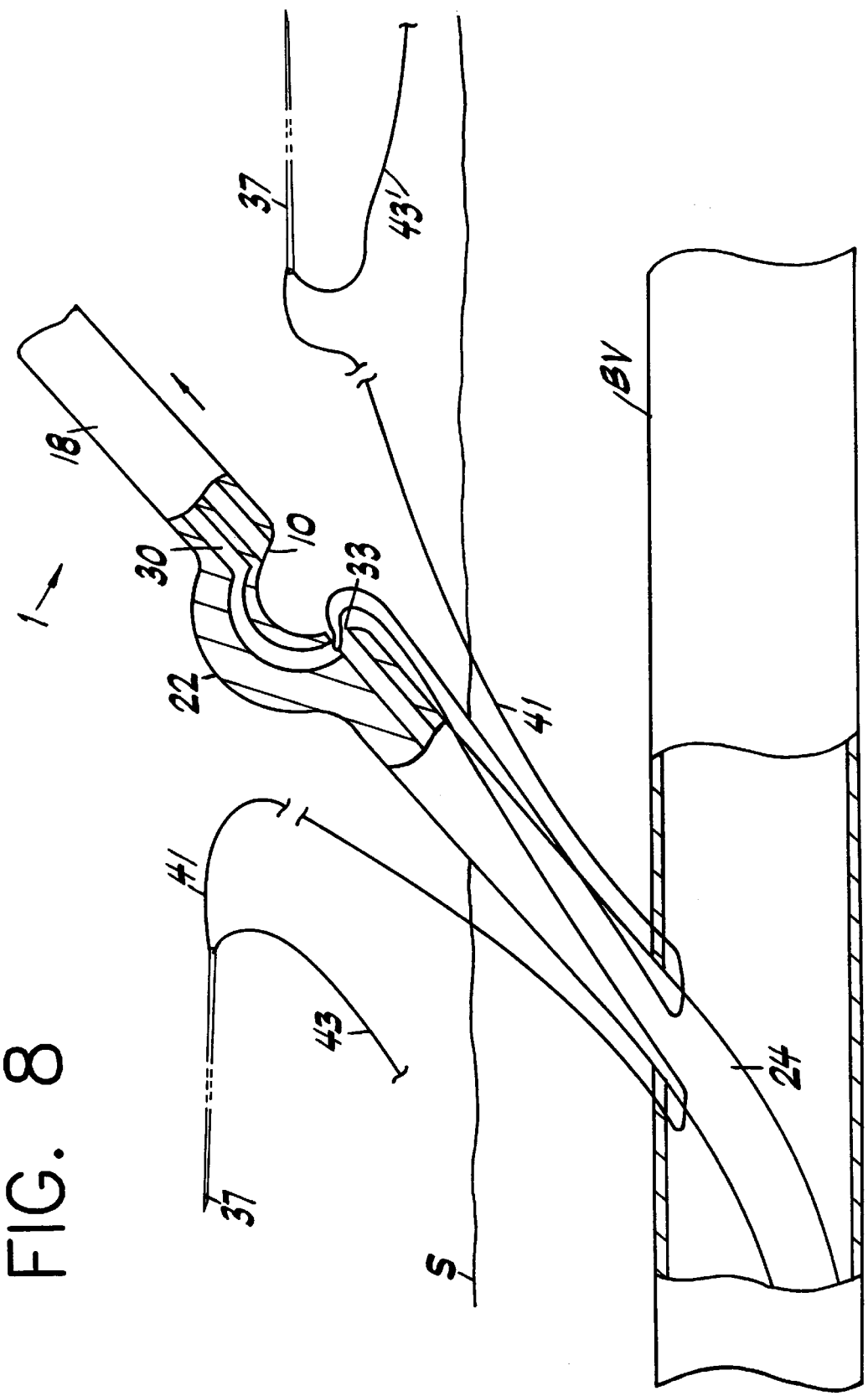
FIG. 8 shows a partially cross-sectional view of the blood vessel with a device according to the first embodiment of the present invention partially removed from the blood vessel.
Figure 9:
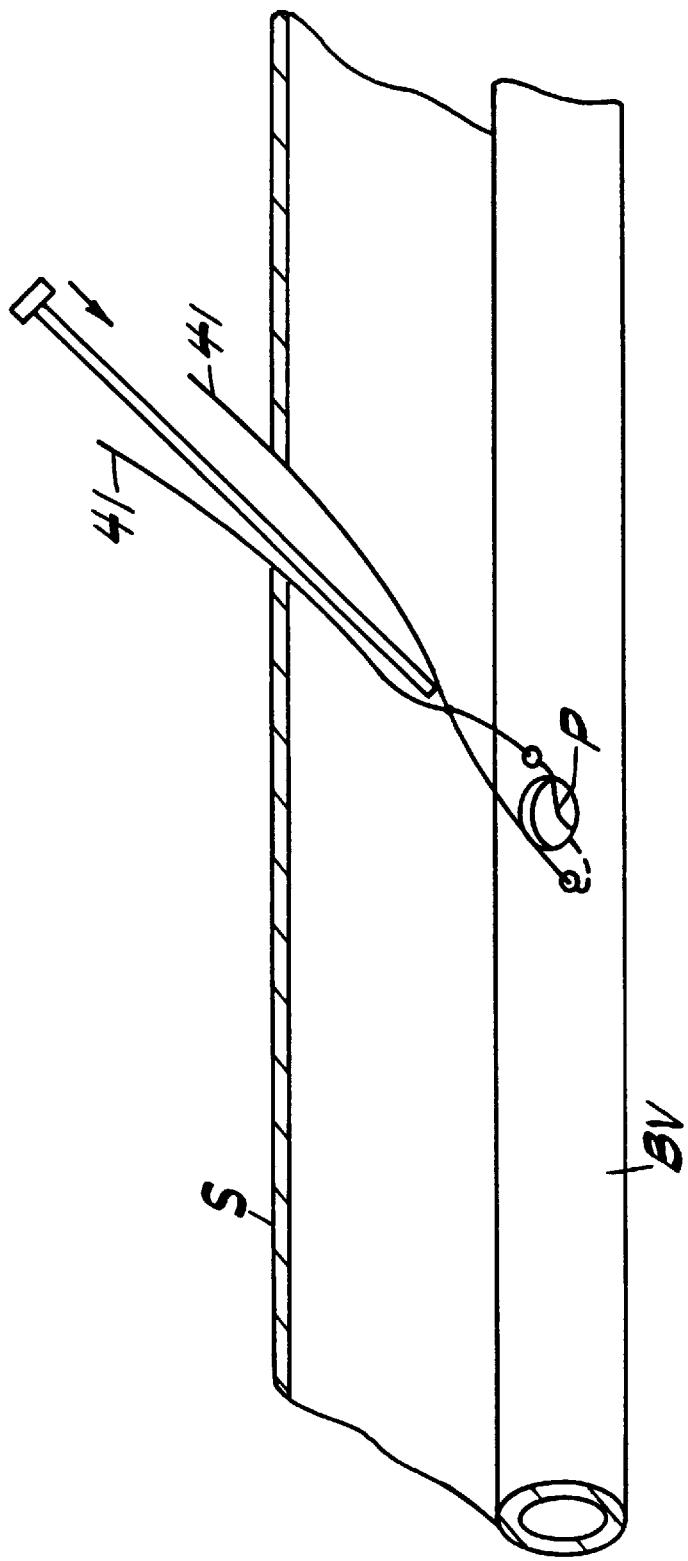
FIG. 9 shows a slip knot tied in a suture loop extending through the wall of the blood vessel being urged toward the blood vessel.
Figure 10:
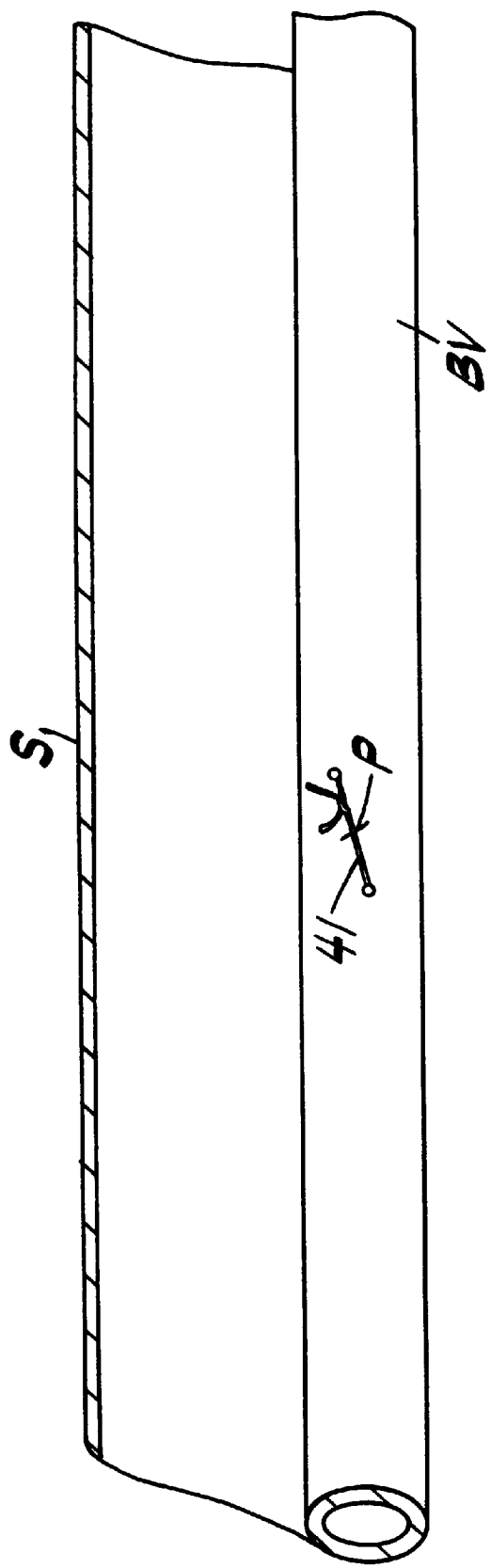
FIG. 10 shows a suture sealing the puncture.
Figure 13:
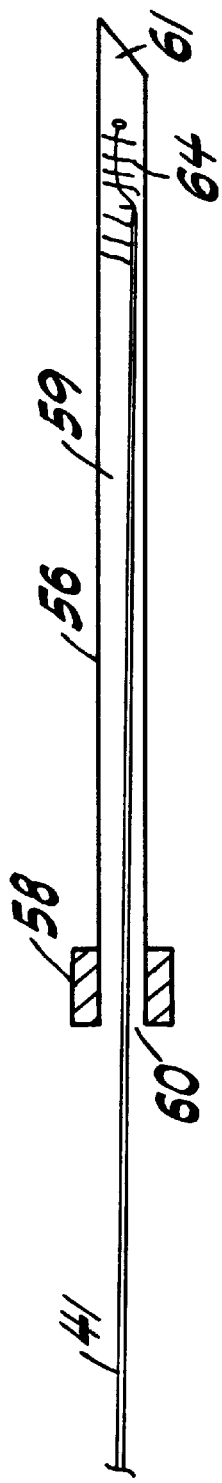
FIG. 13 shows a cross-sectional view of a puncture needle according to the second embodiment of the present invention.
Figure 14:
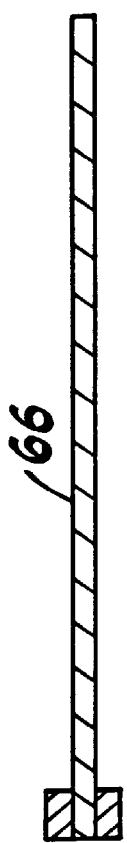
FIG. 14 shows a side view of a plunger according to the second embodiment of the present invention.
Figure 15:
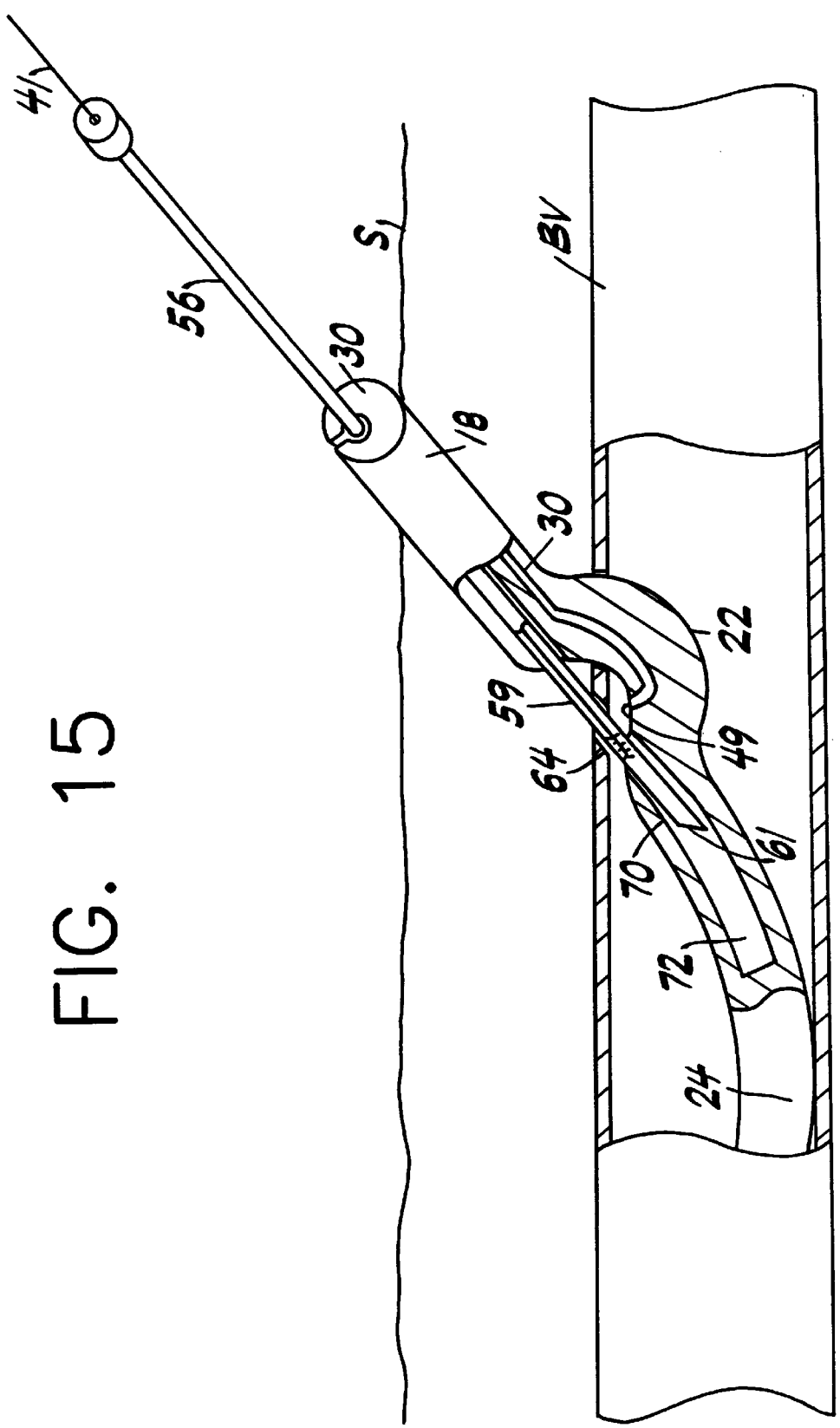
FIG. 15 shows a partially cross-sectional view of the blood vessel with a device according to the second embodiment of the present invention in a first desired position.
Figure 16:
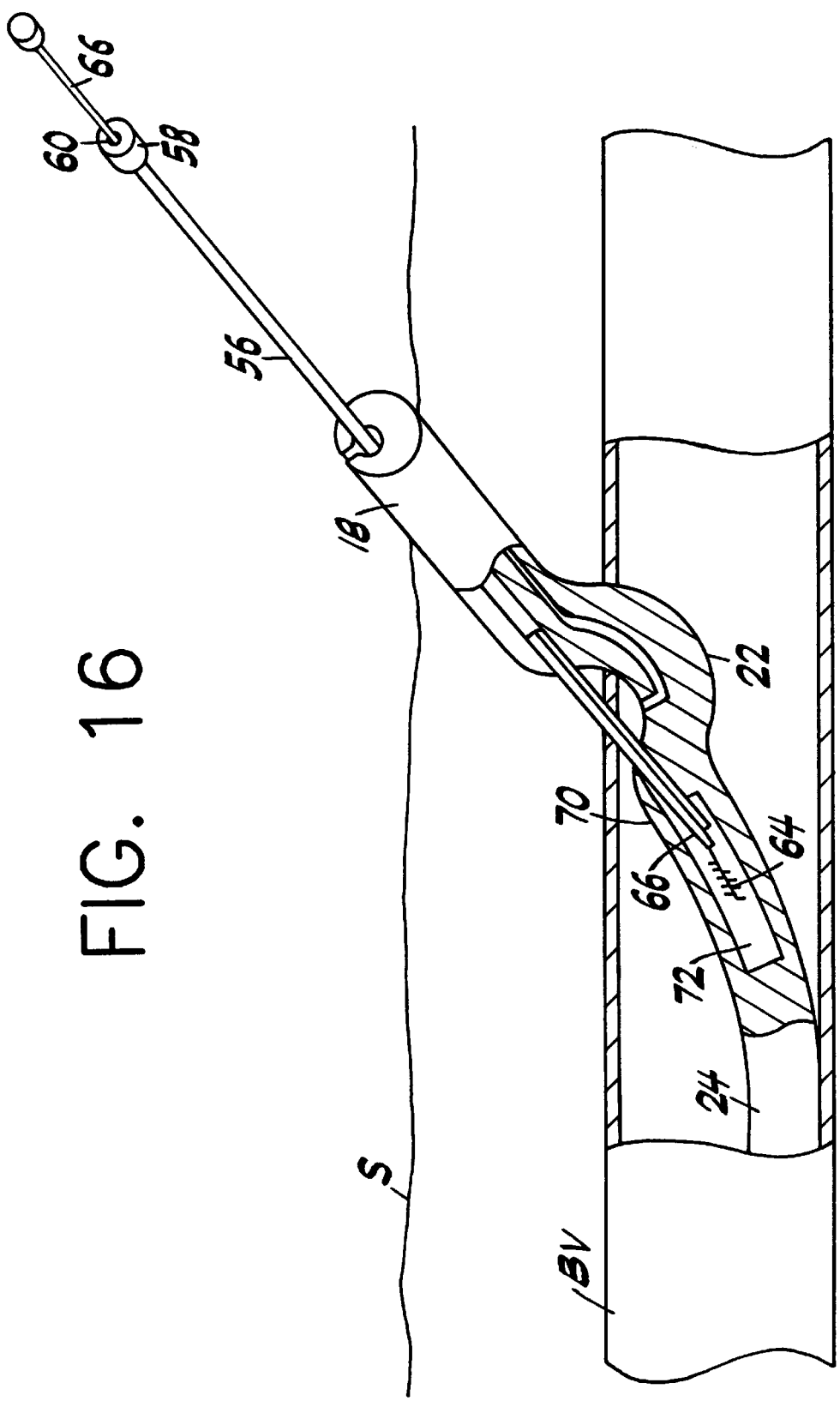
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The flexible tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular puncture needle channel 50 extending from the first end 20 of the device 1' to an opening 52 at a proximal end of the central arcuate portion 22. This puncture needle channel 50 is also shown including an optional slot 54 extending through the surface of the flexible tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically, when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
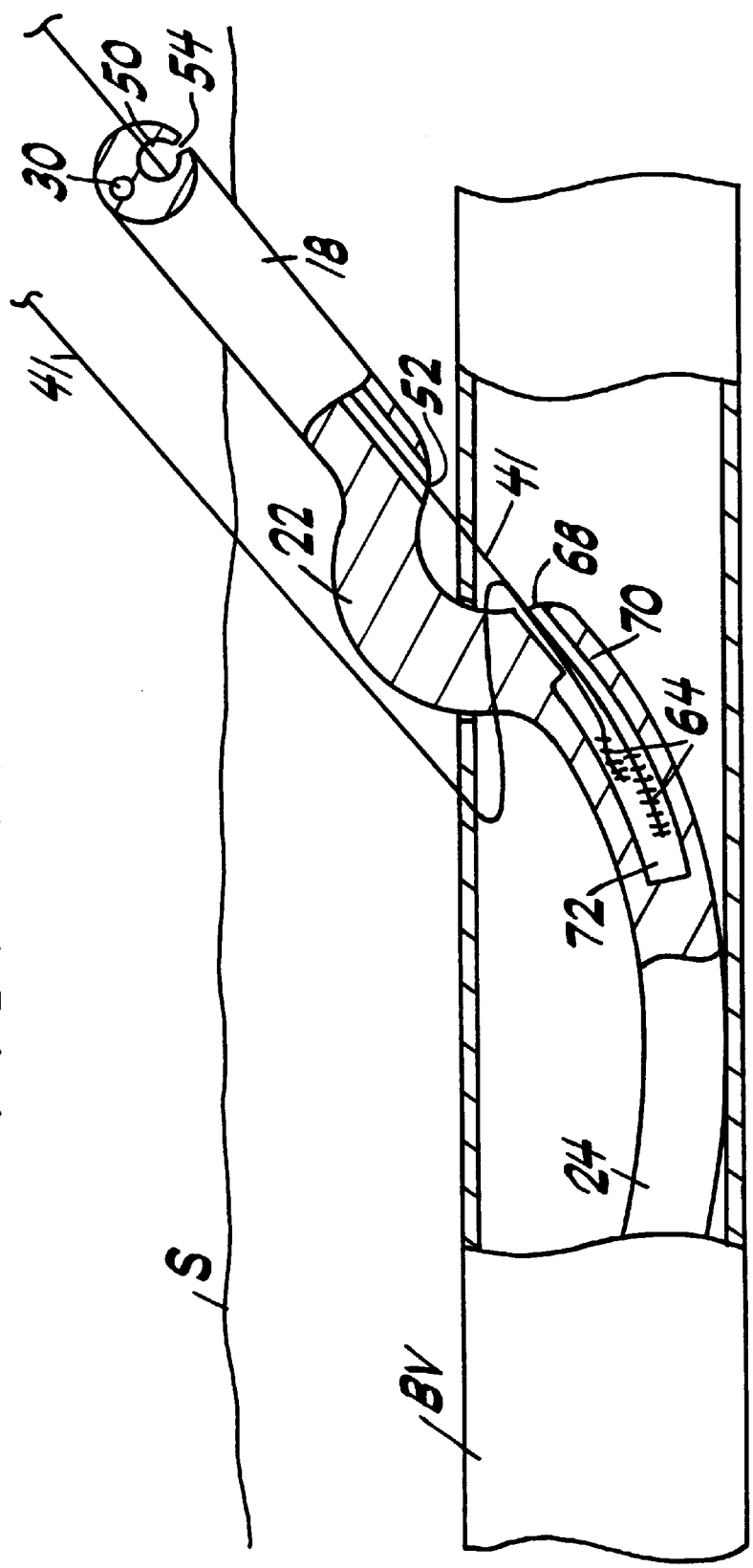
FIG. 17 shows a partially cross-sectional view of the blood vessel with a device according to the second embodiment of the present invention in a second desired position.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

Figure 18:
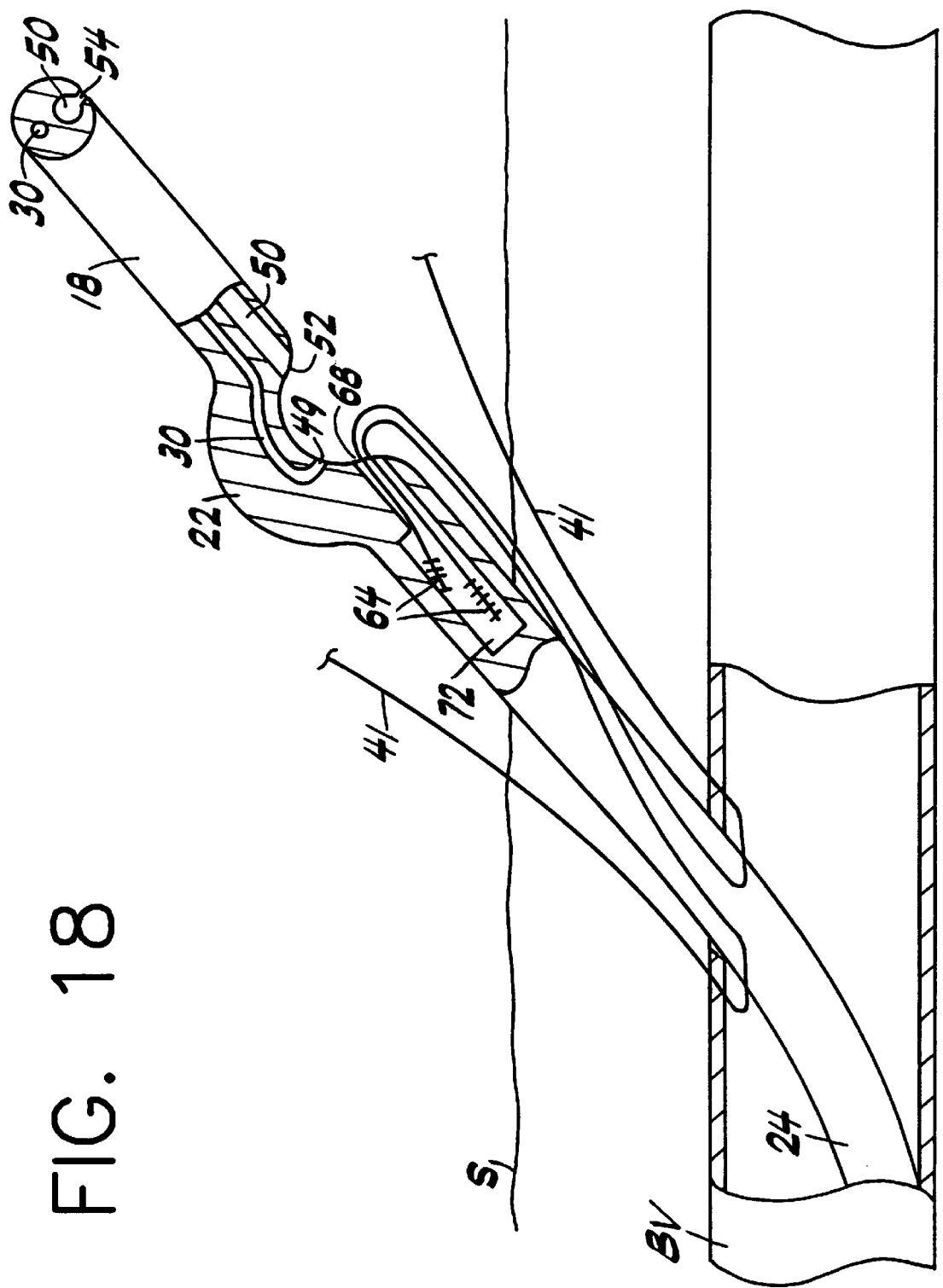
FIG. 18 shows a partially cross-sectional view of the blood vessel wherein the device according to the second embodiment has been partially withdrawn from the blood vessel.
Figure 19:
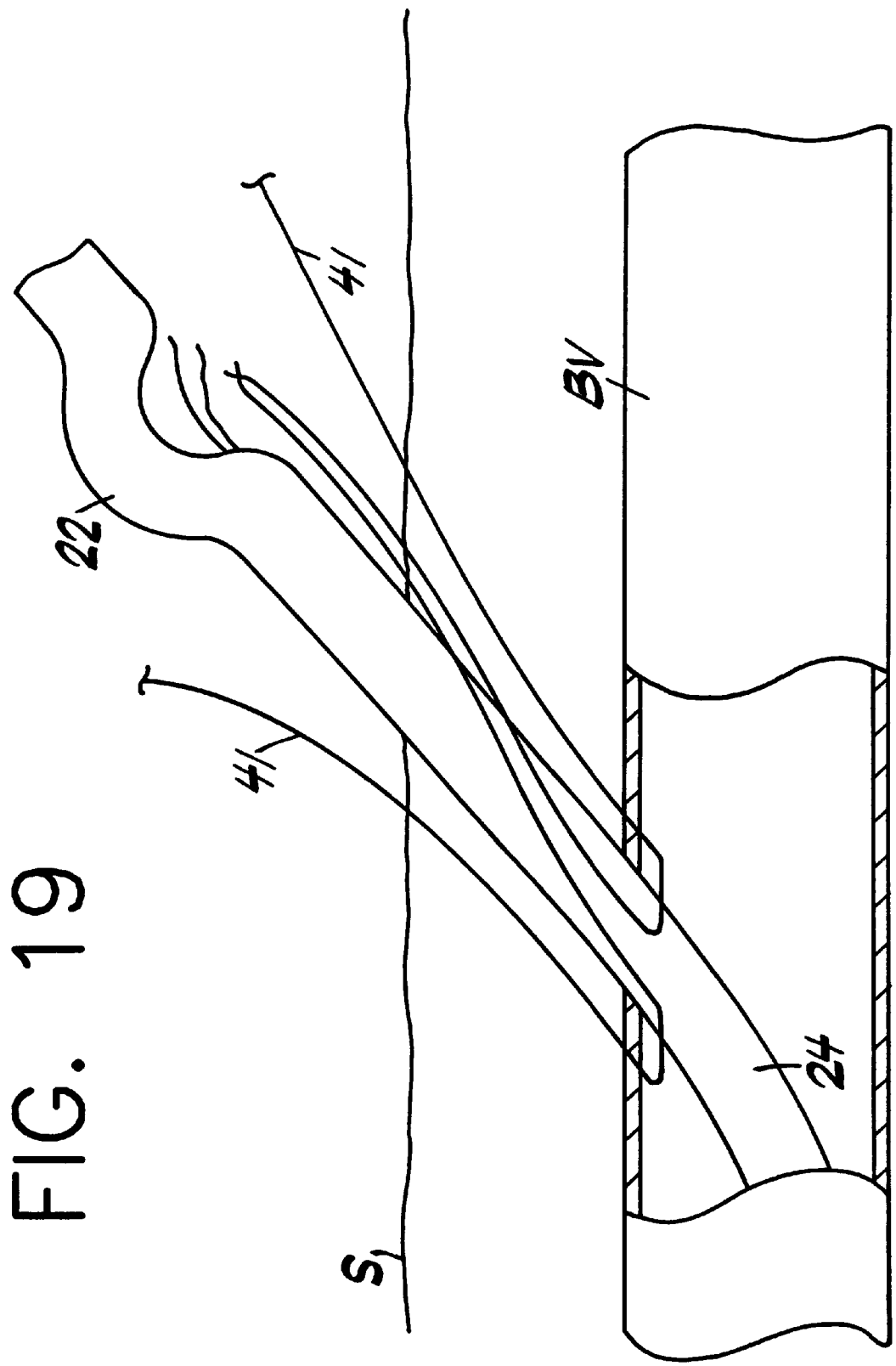
FIG. 19 shows a partially cross-sectional view of the blood vessel wherein the sutures have been severed from the anchor members and tied together.

The doctor then withdraws the device 1' from the body, as shown in FIG. 18, so that the ends of the sutures 41 extending from the opening 68 may be cut to release the sutures from the anchor members 64. Then, as shown in FIGS. 18 and 19, these ends of the sutures 41 are tied together and the other ends are knotted together and tightened to seal the puncture.

Those skilled in the art will understand that, for larger punctures, the device 1" may be used to insert as many sutures 41 as are required to seal the puncture. Specifically, in order to close punctures larger than size 9.0 French, a single suture 41 may not be sufficient. Therefore, instead of using the device 1" as described above to insert two sutures 41 approximately 180° apart, a doctor may, for example, insert four sutures 41 at 90° intervals using the technique described above. Then, when the device 1" has been withdrawn from the body, the doctor must knot together a first pair of sutures 41 which are separated by approximately 180° and then knot the second pair. The two pairs of sutures 41 may be distinguished by color coding or any similar technique.

Figure 20:
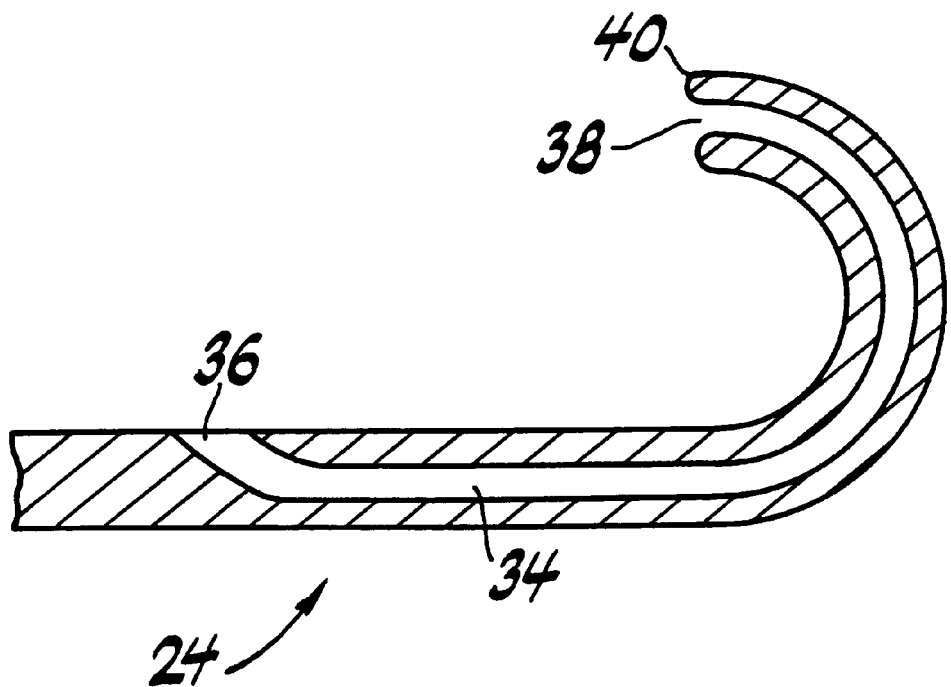
FIG. 20 shows a side view of a cross-section of a distal portion of a suturing device according to a third embodiment of the present invention.

A device 1" according to a third embodiment of the present invention is shown in FIG. 20. Aside from a modified distal part 24 as described below, the construction and operation of the device 1" may be identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
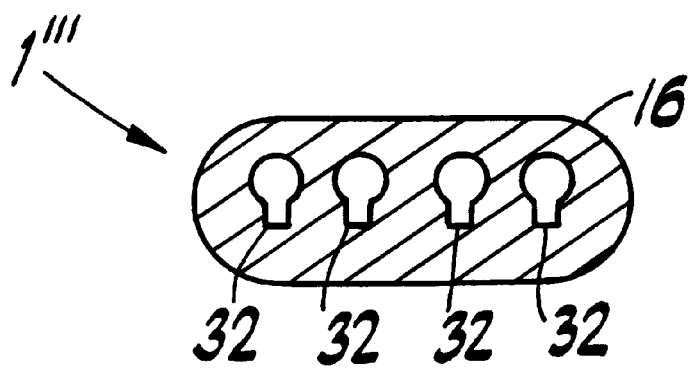
FIG. 21 shows a cross-section of a distal portion of a device according to the fourth embodiment of the invention.
Figure 34:
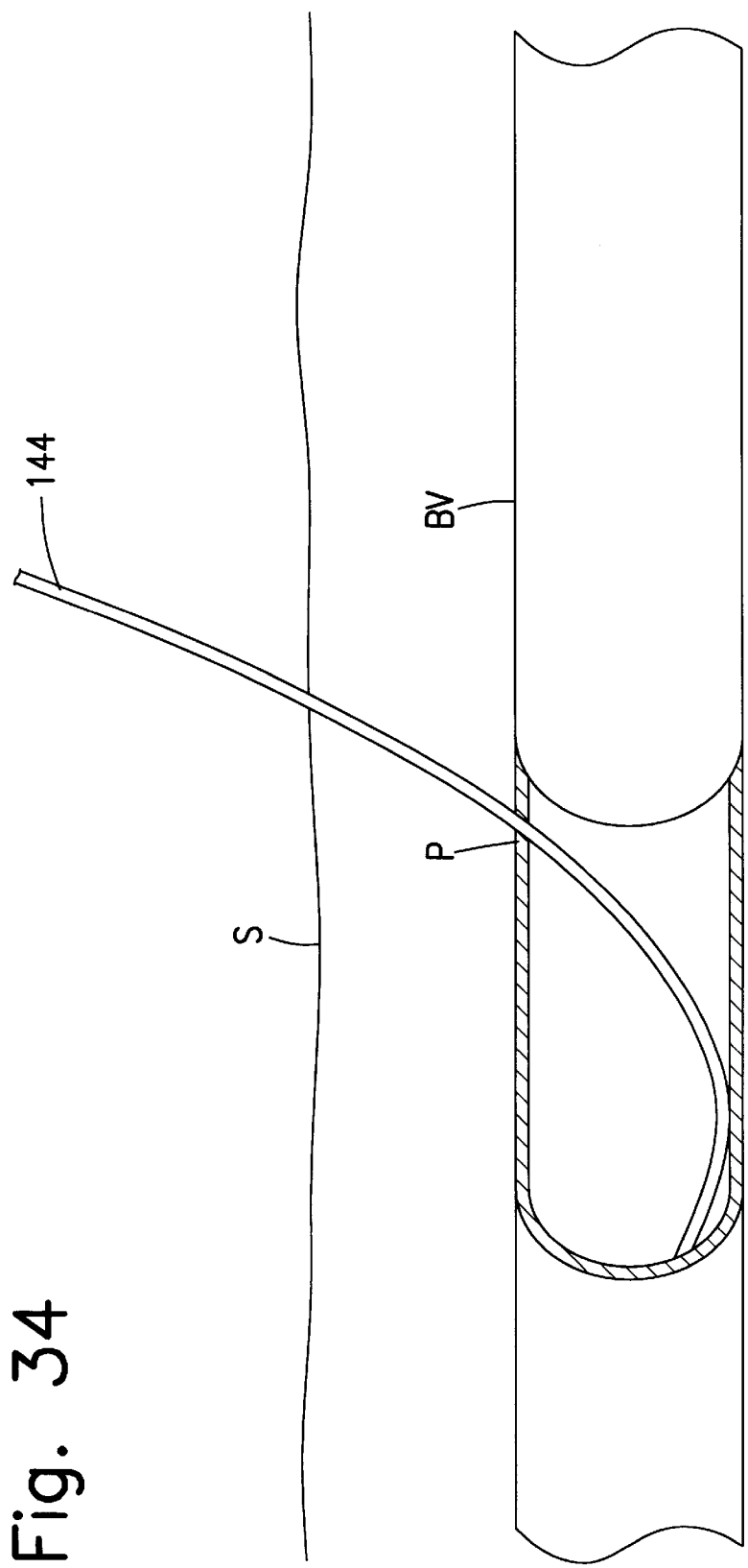
FIG. 34 shows a perspective view of a guide wire inserted into an anatomical structure, specifically a blood vessel.
Figure 35:
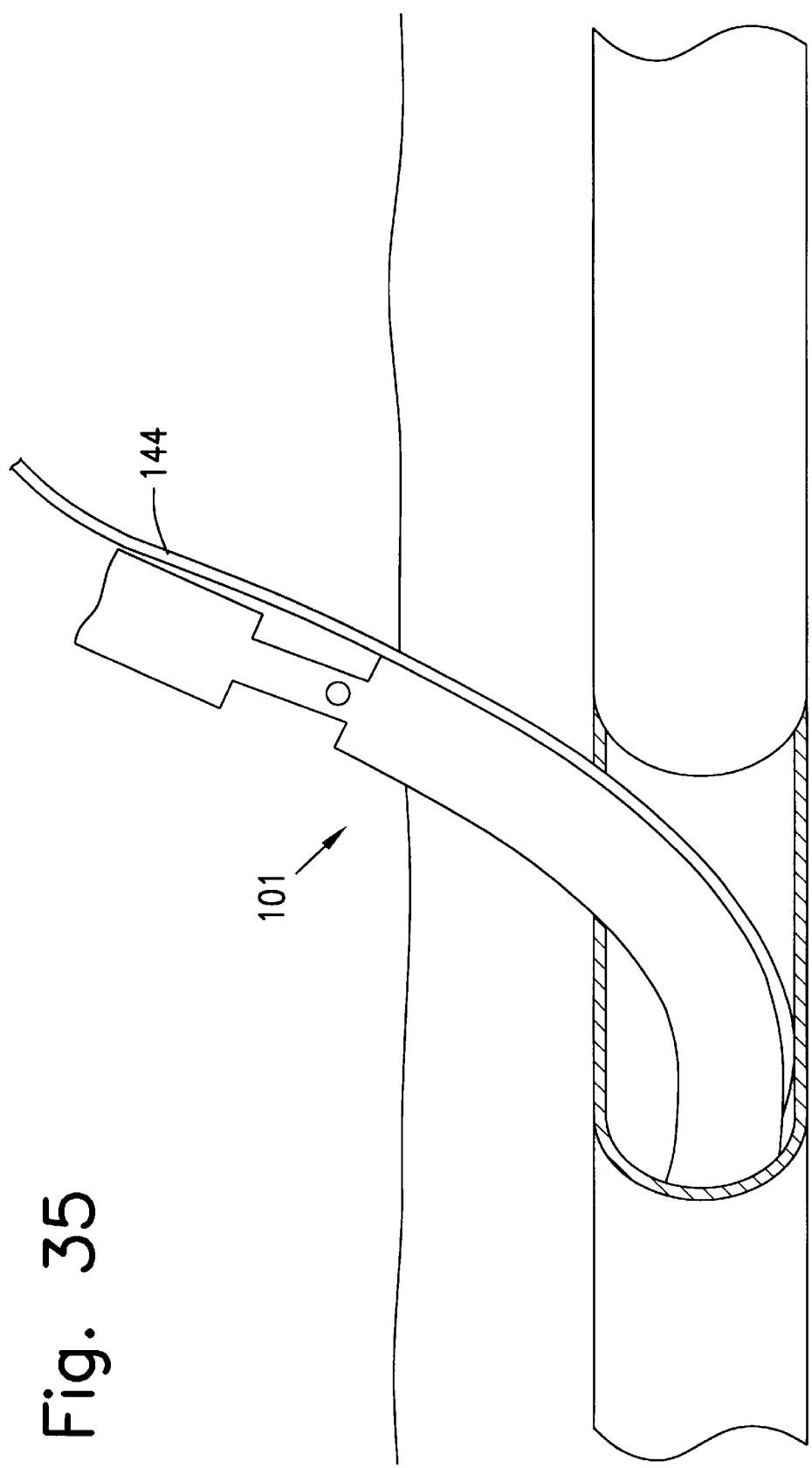
FIG. 35 shows a perspective view of a suture device according to the present invention partially inserted into an anatomical structure.
Figure 36:
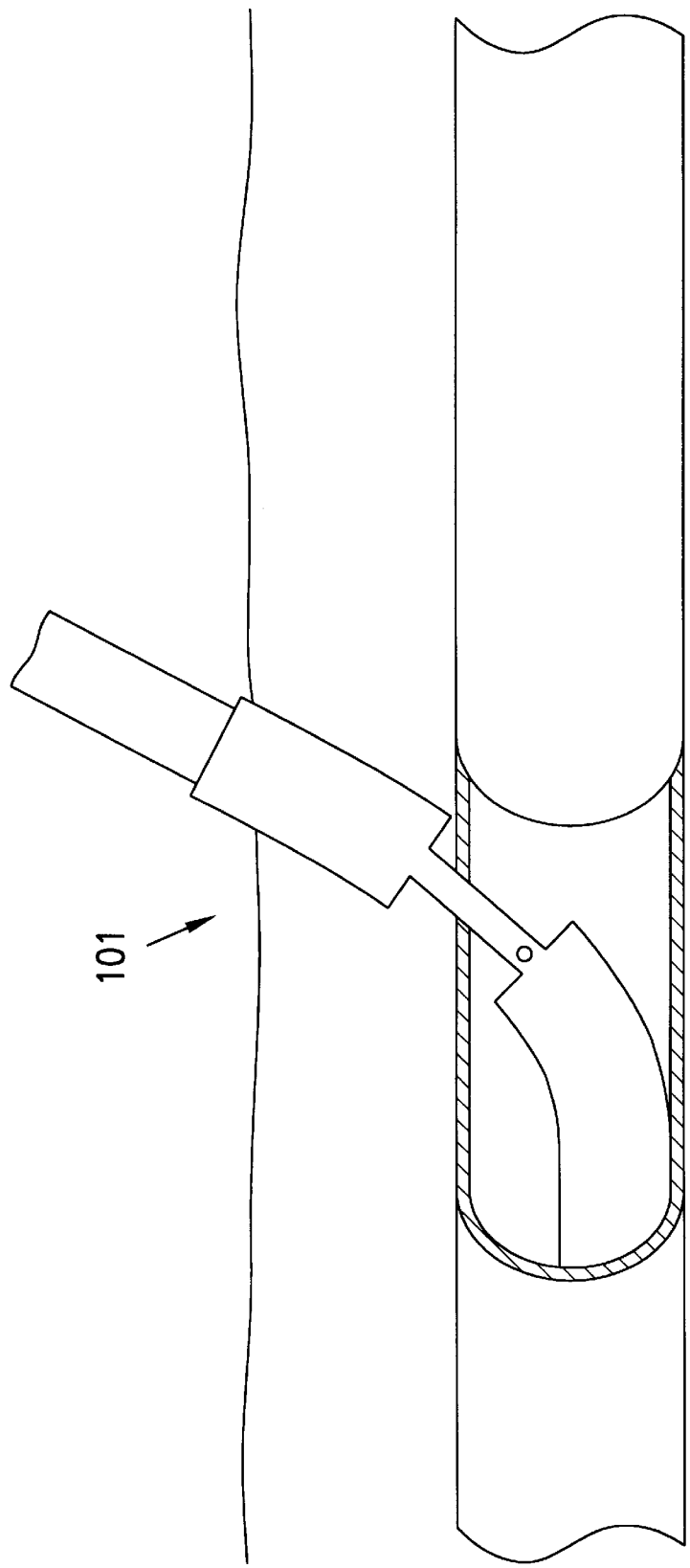
FIG. 36 shows a perspective view of the suture device of FIG. 35 inserted to a desired position in an anatomical structure.
Figure 37:
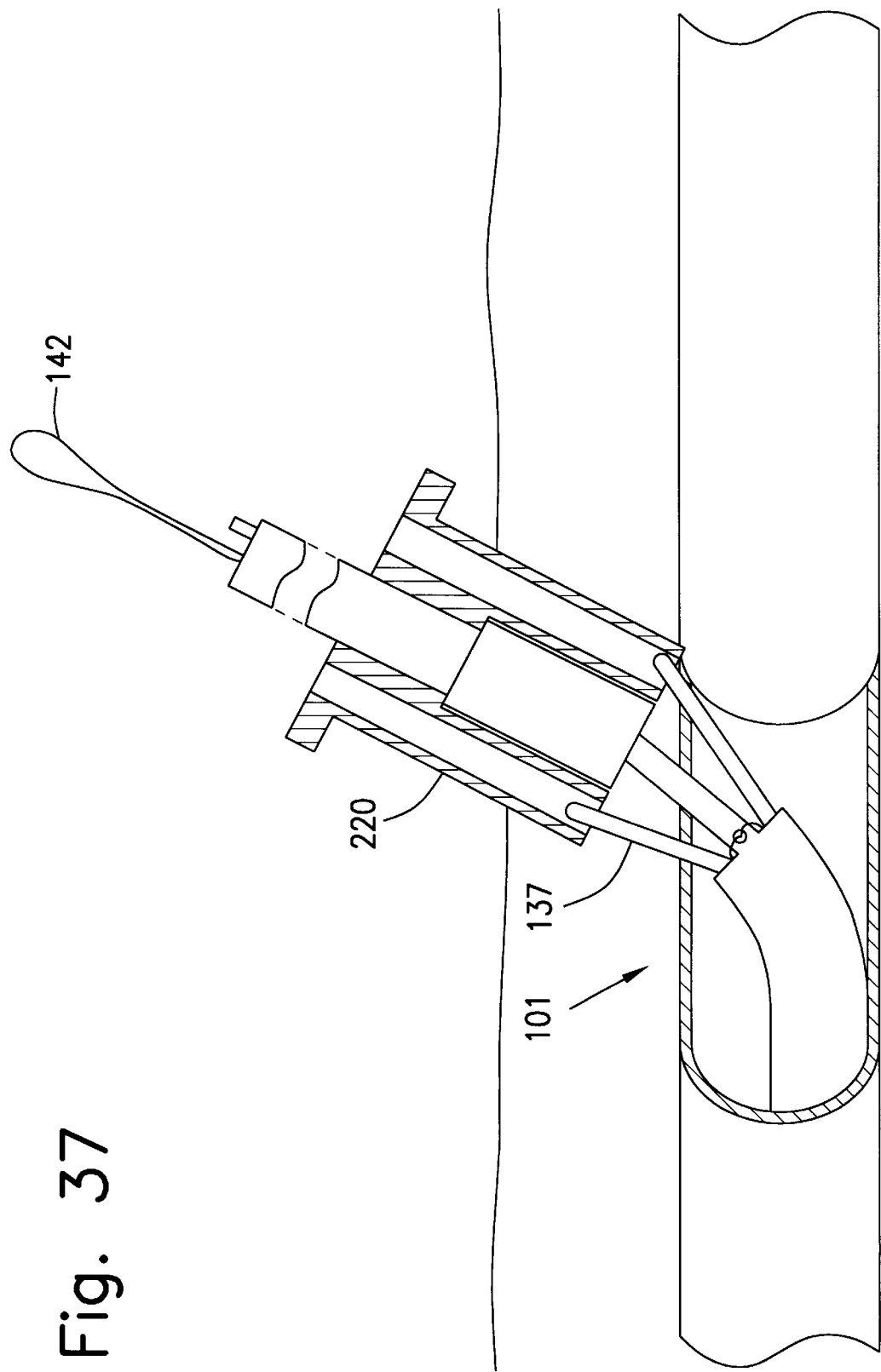
FIG. 37 shows a perspective view of the suture device of FIG. 26 with a needle receiving body according to the present invention.
Figure 38:
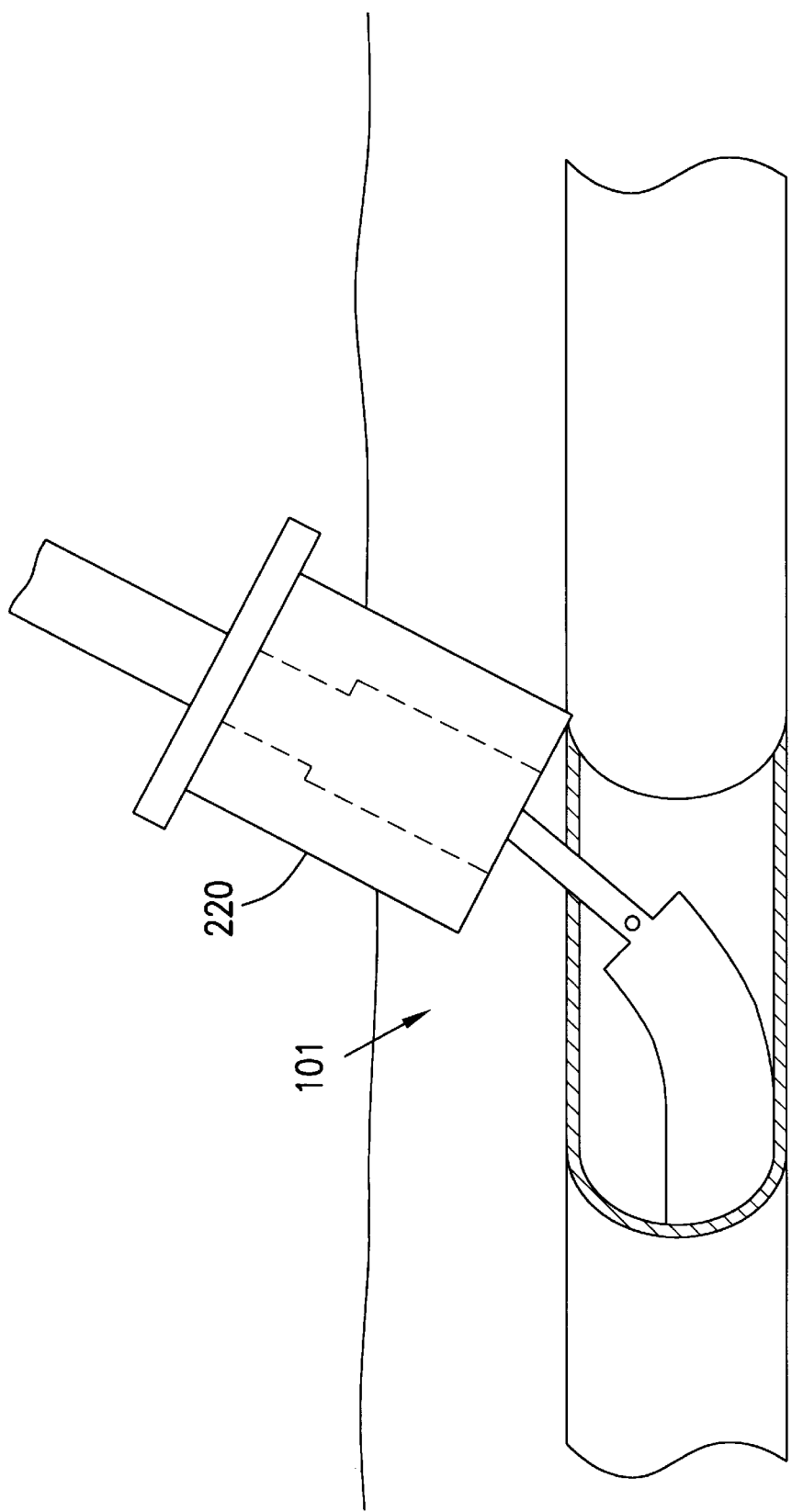
FIG. 38 shows a perspective view of the suture device of FIG. 37 with a pair of puncture needles partially deployed.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a flexible tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1". Similarly, those skilled in the art will recognize that four needles 37 may be received in a device 1''' having two needle retention bores 32, each being of a length sufficient to hold two needles 37 arranged in series end-to-end.

FIG. 22 shows a further embodiment of a suture device 101 according to the present invention. In this embodiment, the needles 137 are deployed simultaneously, eliminating the need to rotate the device 101 within the opening in the anatomical structure. This is achieved with a device 101 formed as an elongated member 116 having proximal portion 118 which may preferably be rigid coupled to a flexible distal portion 124 by, for example, a rigid central portion 122. The proximal portion 118 and the distal portion 124 are both, for example, substantially circular in cross section. A distal end 121 of the proximal portion 118 has, for example, a slightly larger diameter than the rest of the proximal portion 118, forming a stop 221. The central portion 122 is, for example, oval or oblong in cross section. However, the cross-sectional area of the central portion may preferably be substantially equal to that of the distal portion. Moreover, unlike the central arcuate portion 22 of the other embodiments of the device (1, 1", etc.) of the present invention, the central portion 122 may be substantially straight.

As can be seen from FIG. 23, the proximal portion 116 has, for example, a pair of lumens extending axially therethrough: a position indication lumen 200 and a suture lumen 130. The position indication lumen 200 extends from a proximal position opening 201 in a proximal end 120 of the proximal portion 118 to a central position opening 202 in the central portion 122. Of course, those skilled in the art will understand that the central position opening 202 may be located at any position which, when the device is in the operative position, is located within the blood vessel. In the central portion 122, the position indication lumen 200 turns, for example, 90° outward, so that the position indication lumen 200 runs radially outward until it terminates at the central position opening 202.

The suture lumen 130 extends from a proximal suture opening 131 in the proximal end 120 of the proximal portion 118 to a needle chamber 132 disposed in the distal portion 124. The suture lumen 130 is also connected to a central suture opening 203 in the central portion 122. The central suture opening 203 extends radially outward from the suture lumen 130. However, the central suture opening 203 runs, for example, in an opposite direction from the position indication lumen 200, so that the central suture opening 203 and the central position opening 202 are on radially opposite sides of the central portion 122.

Further details of the elongated member 116 are shown in FIG. 25. The distal portion 124 includes, for example, a single, axially-running needle chamber 132 holding, for example, a pair of needles 137. The needles 137 are not fully contained in the needle chamber 132. Instead, part of each needle 137 extends through a needle channel 123.

Each needle channel 123 runs substantially axially from the needle chamber 132 to a needle channel opening 133. However, as can be seen from FIG. 25, each needle channel 123 also runs, for example, slightly radially outwardly as it extends from the needle chamber 132 to the respective needle channel opening 133. The needle channel openings 133 appear on a proximal face 233 of the distal portion 124, and are located, for example, on radially opposite sides of the proximal face 233 of the distal portion 124. Thus as the needles 137 exit the needle channels 123, the needles 137 move substantially in the proximal direction (towards the right as seen in FIG. 25), but also slightly outwardly in opposite radial directions from one another.

In addition to being radially opposite from each other, the needle channel openings 133 are each, for example, radially offset 90° from the central position opening 202 and the central suture opening 203. The needle channel openings 133 are, for example, radially aligned with a minor axis of the oval central portion 122, while the central position opening 202 and the central suture opening 203 are located, for example, on the major axis of the central portion 122.

For example, two segments of a length of suture 141 are contained within the elongated member 116. The length of suture 141 is doubled over itself so that a suture loop 142 extends outside the proximal suture opening 131. Two segments of the length of suture 141 enter the suture lumen 130 via the suture opening 131 and exit the suture lumen 130 via the central suture opening 203. Each of the two segments then enters a respective needle channel 123 and travels ultimately to the needle chamber 132. The end of each segment of the length of suture 141 is connected to the distal end of a respective one of the needles 137 within the needle chamber 132.

As can also be seen from FIG. 25, the device 101 according to this embodiment may be manufactured in three sections: a first section including the proximal portion 118, the central portion 122, and the proximal end of the distal portion 124 containing the needle channels 123; a second section including only that part of the distal portion 124 containing the needle chamber 132; and a third section including only a soft tip 140 at the distal end of the distal portion 124. These various sections may preferably be formed separately, for example by extrusion or molding, and then fixed together.

FIGS. 26, 27 and 28 show cross-sectional views of the device 101 taken along lines 26—26, 27—27, and 28—28 of FIG. 25, respectively. FIG. 26 shows the distal portion 124 with the needle chamber 132 therein. The needle chamber 132 contains, for example, two needles 137, each needle 137 connected to an end of a length of suture 141. FIG. 27 shows the central portion 122 and the proximal face 233 of the distal portion 124. The suture 141 passes from the suture lumen 130 and central suture opening 202 into the needle channel openings 133. FIG. 28 shows the proximal portion 118 with the position indication lumen 201 and the suture lumen 130 therein. The suture lumen 130 contains two segments of a length of suture 141.

A needle receiving body 220 of the device 101 is shown, for example, in FIGS. 29 and 30. The needle receiving body 220 as shown is an elongated member having a generally annular cross section for most of its length. Two protrusions 222 extend, for example, radially outward from a proximal end 221 of the needle receiving body 220. The protrusions 222 assist in handling the needle receiving body 220.

The needle receiving body 220 has a device lumen 225 extending axially therethrough. The device lumen 225 shares, for example, the same axis as the needle receiving body 220 as a whole (i.e. the device lumen 225 is radially centered within the needle receiving body 220). The device lumen 225 has a first inner diameter substantially the same diameter as, or slightly larger than, the outer diameter of the proximal portion 118 and a second inner diameter slightly larger than the first inner diameter so that an abutment 227 is formed at the intersection of the portion having the first inner diameter and the portion having the second inner diameter.

On opposite sides of the device lumen 225 a pair of axially-running needle receiving channels 226 extend. The needle receiving channels 226 are adapted, for example, to receive needles 137 when they are urged out of the needle channels 123.

The inner diameters of the needle receiving body 220 allow it to be slidably placed upon the elongated member 116. The needle receiving body 220 travels down the proximal portion 118, and slides distally until the abutment 227 of the needle receiving body 220 contacts the stop 221 on the elongated member 116. At this point the needle receiving body 220 may be fixedly or rotatably joined to the elongated member 116 (for example, as part of the manufacturing process), or may remain slidably and/or frictionally coupled with the elongated member 116. The latter configuration allows the use of a device 101 without a needle receiving body 220 if so desired, for example when closing skin wounds or during certain laparoscopic procedures.

FIG. 31 shows the tip 140 which is disposed at the distal end of distal portion 124. As seen from the Figure, the tip 140 may be a J-shaped, elongated member. The tip 140 may also, however, be formed as a straight member or any other shape, as dictated by the shape of the anatomical structure and surrounding tissues. The tip 140 includes, for example, an axially-running guide wire lumen 138 extending therethrough. The tip 140 may be formed of, for example, a soft or flexible material. The shape of the tip 140 and its material allow the tip 140 to be easily inserted into the anatomical structure.

The device 101 according to this embodiment of the present invention may also include a knot pusher 300, as shown in FIGS. 32 and 33. The knot pusher 300 includes a longitudinal member 301 having, for example, a circular cross section. A knob 302 is disposed, for example, at a proximal end of the longitudinal member 301. The distal end of the longitudinal member 301 is, for example, rounded.

The distal end of the longitudinal member has an axially-extending slit 303 formed therein. The slit 303 has, for example, a constant width appropriately sized to accommodate one or more segments of a length of suture 141, but small enough so that a knot cannot enter the slit 303. The depth of the slit 303, however, decreases as the slit extends proximally from the distal end of the longitudinal member 301. The slit 303 has an initial depth, for example, slightly greater than the radius of the longitudinal member 301, and the depth decreases to zero, for example linearly, as the slit extends proximally.

The distal end of the longitudinal member 301 also has, for example, a circular recess 304 formed therein. The recess 304 intersects the slit 303, forming a continuous path through the elongated member 301. The recess 304 preferably has a radius greater than the width of the slit 303, and should generally be sized to accommodate a knot in the length of suture 141. Thus a knot in a length of suture 141 may be inserted into the recess 304 and that one end of the length of suture 141 pulled through the slit 303 to tighten the knot.

The operation of the device 101 according to this embodiment is shown in FIGS. 34–41. When an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 144 is inserted through the puncture to a target area within the blood vessel and a catheter is inserted through the introducer sheath, along the guide wire 144, to a target area within the blood vessel.

After the procedure is complete, the catheter and the introducer sheath are withdrawn and the guide wire 144 is, for example, left in place. A proximal end of the guide wire 144 is then inserted, for example, through the guide wire lumen 138 and the device 101 is inserted into the body and moved along the guide wire 144 through the puncture until the central portion 122 is located within the puncture (i.e. the walls of the blood vessel on opposite sides of the puncture surround the central portion 122). The major axis of the central portion 122 should be aligned with the length of the puncture so that the wall around the puncture is stretched as little as possible.

By observing the position indication lumen 201, the doctor may determine when the device 101 is in the desired position. Specifically, when the device 101 is inserted far enough into the blood vessel, blood will begin to be observed in the position identification lumen.

As the device 101 is inserted into the blood vessel, the flexible tip 140 bends so that the device 101 is received within, and extends in the direction of the blood vessel without straining the vessel. In this position, the needle channels 123 are inside the blood vessel with the needles facing proximally, that is, toward the proximal portion 118.

If desired, the needle receiving body 220 may then be introduced around the proximal portion 118 and slid down the proximal portion 118 until it reaches the stop 221. The needle receiving body 220 may also be rotated, if necessary, to align the needle receiving lumens 226 with the needle channel openings 133 (when the needle receiving body 220 is not fixedly attached to the elongated member 116).

With all the components of the device 101 in place, the operator may pull on the loop 142 in the length of suture 141. As the suture is withdrawn through the elongated member 116, it pulls the needles 137 out of the needle chamber 132 and the needle channels 123. The needles 137 penetrate the wall of the blood vessel on opposite sides of the puncture and enter the needle receiving lumens 226, if present. The needles 137 should be of sufficient length so that, when the suture loop is drawn out of the elongated member 116, the proximal ends of the needles 137 exit the proximal end of the needle receiving body 220.

Figure 39:
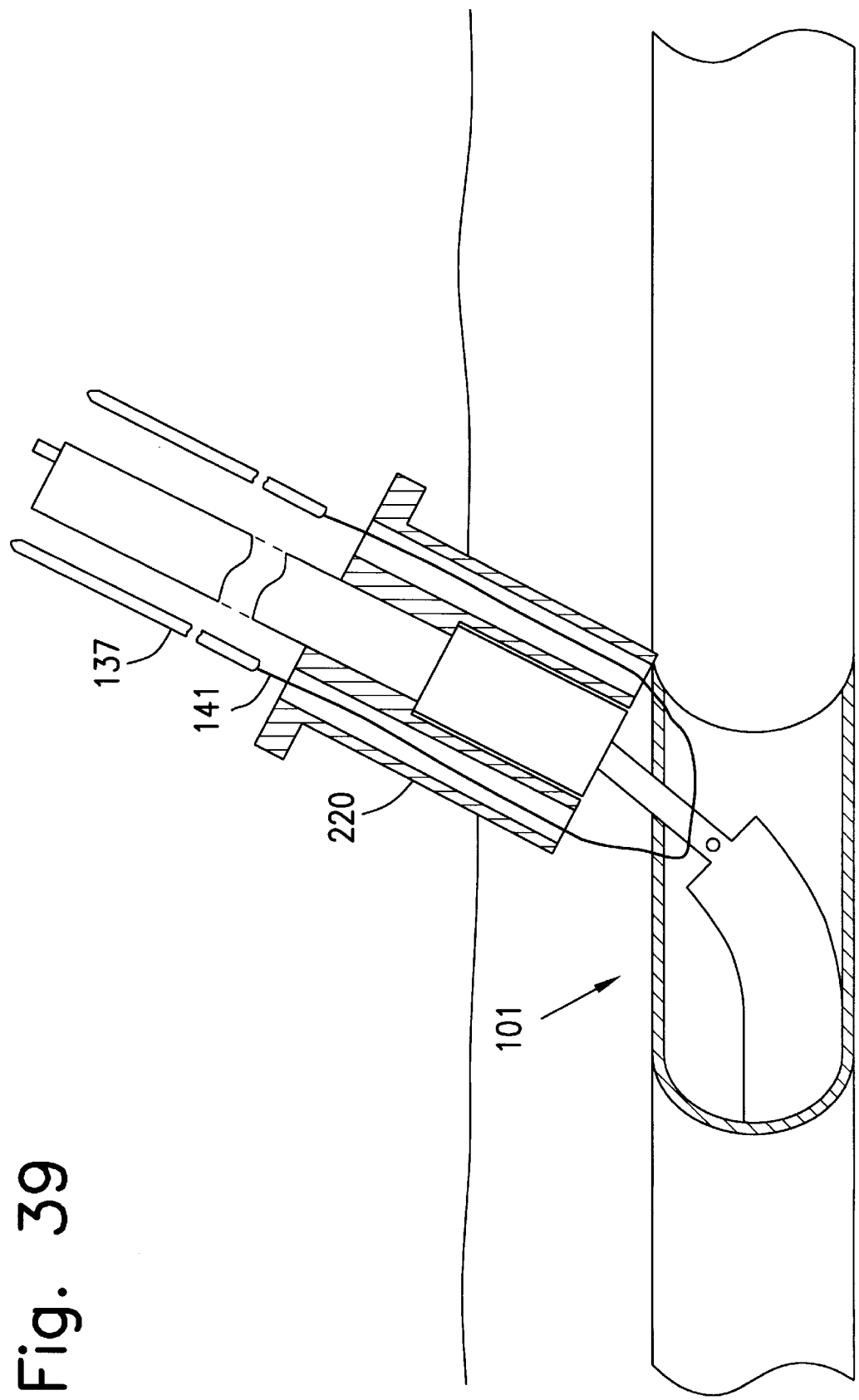
FIG. 39 shows a perspective view of the suture device of FIG. 38 with the pair of puncture needles fully deployed and a length of suture spanning the opening in the anatomical structure.
Figure 40:
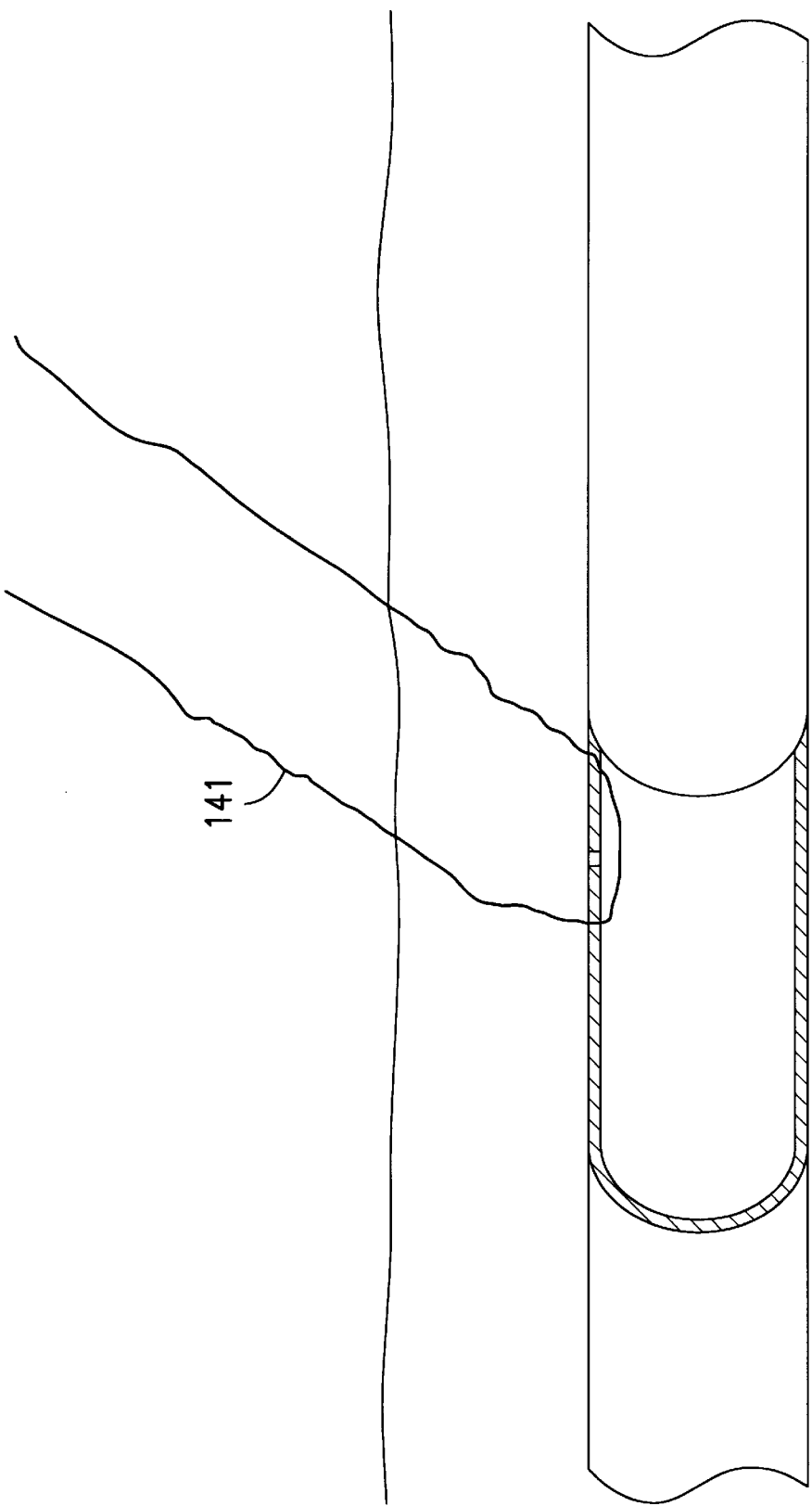
FIG. 40 shows a perspective view of a length of suture after being detached from a suture device according to the present invention.

The operator may then grasp the needles 137 and pull them through the blood vessel wall and through the needle receiving body 220, thereby pulling the loop 142 of the length of suture 141 distally through the suture channel 130 and into the blood vessel, as shown in FIG. 39. The length of suture 141 may then be separated from the needles 137 and withdrawn from the needle receiving body 220. After the length of suture 141 is knotted, the knot pusher 300 may be used to tighten the knot, thereby sealing the puncture.

An additional feature of the device 101 according to the present invention is shown in FIG. 42. The needles 137 may be removably implanted in a platform 150 disposed within the needle chamber 132. The platform 150 allows the user to push the needles 137 back into the needle chamber 132 after they have been partially deployed by inserting a rod (not shown) into the suture lumen 130 and the needle chamber 132. The rod can be used to push the platform 150 distally, moving the needles 137 likewise distally, back to their initial position. This feature is useful if, for example, the length of suture 141 breaks prior to complete deployment or one of the needles 137 meets an obstruction.

FIG. 44 illustrates a further exemplary embodiment of the present invention. In this embodiment, the position indication lumen 200 is shaped, for example, to house a retractable anchor 160 and an anchor control arm 162. In particular, the portion of the position indication lumen 200 extending radially outward may, for example, be slanted backward (i.e. proximally) toward the central position opening 202.

Control arm 162 extends axially, for example, through the axial portion of position indication lumen 200, as shown in FIG. 44, exiting the proximal position opening 201. Anchor 160 may be attached to the control arm 162 near a distal end of the control arm 162. Anchor 160 may be at least partially retained, for example, in the backward-slanting section of position indication lumen 200.

In an exemplary embodiment, anchor 160 is a flexible member. In an unbiased configuration, the end of the anchor 160 may form a curved anchor hook 164. This unbiased configuration may be obtained, for example, when the anchor hook 164 is outside the position indication lumen position indication lumen 200 as shown in FIG. 44. When the anchor hook 164 is within the position indication lumen 200, the interior wall of the position indication lumen biases the anchor hook 164 to a substantially straight configuration.

It can be understood that the control arm 162, and the anchor 160 are capable of movement between a retraced position and an extended position. In the retracted position, the control arm 162 projects distally into the position indication lumen 200 so that anchor 160, including anchor hook 164, are retracted into the position indication lumen 200. Several features may be employed to limit the distal movement of the control arm 162, if desired. For example, a control arm stop 166 may be attached to the portion of control arm outside the suture device 101. The control arm stop 166 will contact the distal end of the suture device 101 when the control arm 160 reaches a distal-most position. Similarly, the distal end of control arm 162 may contact a distal end face of the position indication lumen 200, preventing further distal movement of the control arm 162. Alternatively, the diameter of the control arm 162 may increase moving away from the distal end, so that the wider-diameter section of the control arm 162 is prevented from entering a distal portion of the position indication lumen 200 having a smaller diameter. Other configurations are possible, and any suitable arrangement may be employed if desired.

When the control arm 162 is drawn to the extended position, the anchor 160 extends outside the central position opening 202, and the anchor hook returns to a curved, unbiased configuration.

In practice, the anchor 160 may work in conjunction with, or as an alternative to, the position indication lumen 200. The suture device 101 may be inserted into the body with the control arm 162 and anchor 160 in, for example, the retracted position. As the device 101 approaches the desired position, the control arm 162 and anchor 160 may be moved to the extended position, so that the anchor hook 164 contacts the outside of the blood vessel and retains the suture device 101 in the desired position. Once the blood vessel has been suture as described above, the anchor 160 may be retracted and the suture device 101 removed from the body.

Although the illustrated embodiment of the present invention employs a single length of suture 141 and a single pair of needles 137, those skilled in the art will understand that simple modifications (e.g. the addition of more needle channels 123, etc.) allow the deployment of four or more needles simultaneously. Likewise, there are many other variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A device for sealing an opening in an anatomical structure within a living body comprising:
    a longitudinal member including:
        a proximal portion extending from a proximal portion proximal end to a proximal portion distal end, the proximal portion having a longitudinal suture channel extending therethrough;
        a central portion extending from a central portion proximal end coupled to the proximal portion distal end to a central portion distal end, wherein the suture channel extends through the central portion to a suture opening formed in the central portion distal end; and
        a distal portion extending from a distal portion proximal end coupled to the central portion distal end to a distal portion distal end, wherein a plurality of needle channels extend substantially longitudinally therethrough from the distal portion proximal end;
    a plurality of needles, wherein, in an initial position, each of the needles is at least partly disposed within a respective one of the plurality of needle channels; and
    a length of suture forming a suture loop and a plurality of suture segments each having a suture end, wherein each of the suture segments extends through the suture lumen, the suture opening, and a respective one of the plurality of needle channels, and wherein each of the suture ends is connected to a distal end of a respective one of the plurality of needles so that, when the suture loop is pulled in a proximal direction, the length of suture pulls each of the needles to which the length of suture is coupled from the initial position to a deployed position in which proximal ends of each of the needles coupled to the length of suture extend outside the corresponding needle channels.

2. The device according to claim 1, wherein the distal portion includes a needle chamber extending distally, substantially longitudinally therein from a needle chamber proximal end connected to a distal end of each of the plurality of needle channels, and wherein, when in the initial position, each of the needles is located substantially within the needle chamber.

3. The device according to claim 2, wherein the suture lumen extends through the central portion and the distal portion proximal end, and wherein the suture lumen is connected to the needle chamber proximal end, wherein the distal end of each of the plurality of needles is removably embedded in a platform so that, when in a position between the initial position and the deployed position, pushing the platform distally returns the needles to the initial position.

4. The device according to claim 1, wherein the distal portion distal end includes a flexible tip.

5. The device according to claim 4, wherein the flexible tip is substantially J-shaped.

6. The device according to claim 4, wherein the flexible tip includes a longitudinal guide lumen extending at least partially therethrough.

7. The device according to claim 1, wherein a position indication lumen extends from the proximal portion proximal end through the central portion to a central indication opening located distally of the proximal portion distal end so that, when the device is delivered into the anatomical structure, a body fluid enters the position indication lumen when the device reaches a desired position.

8. The device according to claim 7, wherein the position indication lumen includes an axial portion and a radial portion, further comprising:
    an anchor at least partially contained within the radial portion, the anchor including an anchor hook, the anchor hook being curved in an unbiased configuration; and
    a control arm at least partially contained within the axial portion and partially extending outside a proximal opening in the axial portion, the control arm being connected to the anchor near a distal end of the control arm;
    wherein when the control arm is advanced distally into the axial portion, the anchor moves to a retracted position within the position indication lumen, and when the control arm is drawn proximally from the position indication lumen, the anchor moves to an extended position in which the anchor hook is outside the position indication lumen.

9. The device according to claim 8, wherein the radial portion of the position indication lumen extends partially in a proximal direction as it extends radially outward.

10. The device according to claim 9, wherein the control arm includes a control arm stop disposed on a portion of the control arm outside the proximal opening in the axial portion, so that as the control arm is advanced distally with respect to the position indication lumen, contact between the control arm stop and the proximal portion proximal end defines a maximum amount of advance of the control arm distally within the position indication lumen.

11. The device according to claim 8, wherein when the control arm is advanced distally with respect to the position indication lumen, contact between the distal end of the control arm and a distal end face of the position indication lumen defines a maximum amount of advance of the control arm distally within the position indication lumen.

12. The device according to claim 8, wherein a diameter of a distal portion of the control arm is reduced with respect to a diameter of a proximal portion thereof and wherein a diameter of a distal portion of the position indication lumen is reduced with respect to a diameter of a proximal portion thereof, so that as the control arm is advanced distally with respect to the position indication lumen, contact between an increased diameter proximal portion of the control arm and a decreased diameter distal portion of the position indication lumen defines a maximum amount of advance of the control arm distally within the position indication lumen.

13. The device according to claim 1, wherein the proximal portion further includes a stop, wherein a stop outer diameter is increased with respect to a normal outer diameter of a part of the proximal portion extending proximally of the stop.

14. The device according to claim 13, further comprising:
    a needle receiving body having a device lumen and a plurality of needle receiving lumens extending therethrough, the device lumen including a device lumen proximal part having a first inner diameter and a device lumen distal part having a second inner diameter slightly larger than the first inner diameter so that an abutment is formed at the intersection of the device lumen proximal part and the device lumen distal part, wherein the proximal portion is sized so that it is slidably insertable into the device lumen and may slide through the device lumen until the abutment of the device lumen contacts the stop; and wherein, when moved between the initial and deployed positions, proximal ends of each of the needles enter respective ones of the needle receiving lumens.

15. The device according to claim 14, wherein the needle receiving body is rotatably connected to the proximal portion.

16. The device according to claim 15, wherein, when the needle receiving body is in a position in which the abutment contacts the stop, the needle receiving body is rotatable with respect to the proximal portion and, when the needle receiving body is separated from the position in which the abutment contacts the stop, the needle receiving body is non-rotatable with respect to the proximal portion.

17. The device according to claim 14, wherein the needle receiving body further includes at least one radial protrusion disposed on a proximal end of the needle receiving body.

18. The device according to claim 2, wherein a position indication lumen extends from the proximal portion proximal end through the central portion to an indication opening located distally of the proximal portion distal end so that, when the device is delivered into the anatomical structure, a body fluid enters the position indication lumen when the device reaches a desired position, and wherein the position indication lumen is coupled to the needle chamber and wherein each of the plurality of needles is removably coupled to a needle platform so that, when the needles are in a position between the initial position and the deployed position, pushing the platform distally retracts the needles to the initial position.

19. The device according to claim 1, wherein the proximal portion includes at least one needle receiving lumen extending therethrough to the proximal portion distal end.

20. The device according to claim 1, wherein at least one needle receiving lumen is rotatably coupled to the proximal portion.

21. A method for sealing an opening in an anatomical structure, comprising the steps of:

guiding a device into an opening in an anatomical structure, wherein the device includes:
a longitudinal member including:
a proximal portion including a substantially longitudinal suture channel extending therethrough from a proximal portion proximal end to a proximal portion distal end;
a central portion extending from a central portion proximal end coupled to the proximal portion distal end to a central portion distal end, wherein the suture channel extends through the central portion to a suture opening formed in the central portion distal end; and
a distal portion extending from a distal portion proximal end coupled to the central portion distal end to a distal portion distal end, wherein a plurality of longitudinal needle channels extend distally within the distal portion from the distal portion proximal end;
a plurality of needles, each needle being at least partly disposed within a respective one of the plurality of needle channels; and
a length of suture forming at least one suture loop between respective suture ends, wherein the suture loop extends through the suture lumen, the suture opening, and a respective one of the plurality of needle channels, and wherein each of suture ends is connected to a distal end of a respective needle;

positioning the device so that the distal portion is received within the anatomical structure and the proximal portion is outside the anatomical structure, so that a portion of a wall of the anatomical structure is received between the proximal and distal portions;
drawing the suture loop proximally to draw the needles coupled to the suture ends through the wall of the anatomical structure;
grasping and drawing proximally proximal ends of the needles coupled to suture ends to draw the suture loop distally through the suture lumen into the anatomical structure;
separating the suture ends from the needles;
fastening the ends of the suture loop together to form a knot; and
tightening the knot to seal the opening in the length of suture.

22. The method according to claim 21, wherein the step of guiding a device into an opening in an anatomical structure includes inserting the device into the anatomical structure along a previously inserted guide wire.

23. The method according to claim 21, wherein the device further includes a needle receiving body disposed on the proximal portion of the elongated member, the needle receiving body having a plurality of needle receiving lumens extending therethrough;

wherein the step of drawing needles through the wall in the anatomical structure includes drawing each of the needles at least partially through a respective one of the needle receiving lumens; and wherein the step of grasping and drawing the needles to draw the suture loop into the anatomical structure includes pulling each needle through the respective one of the needle receiving lumens.

24. The method of claim 21, wherein the central portion has a central position opening formed therein and wherein the elongated member includes a position indication lumen extending from the proximal end of the proximal portion to the central position opening; and wherein the step of positioning the device includes urging the device into the anatomical structure until a body fluid enters the position indication lumen.

25. A knot pusher for a length of suture spanning an opening, comprising:

a longitudinal member having a distal face formed thereon, wherein a longitudinal slit extends proximally from a longitudinal slit distal end formed in the distal face for receiving a segment of a length of suture, wherein a depth of the longitudinal slit decreases from a maximum at the longitudinal slit distal end to a minimum at a longitudinal slit proximal end, wherein a recess connected to the longitudinal slit is formed in the distal face for receiving a knot located along the length of suture so that, when a knot is received in the recess and a segment of a length of suture is drawn distally through the longitudinal slit, the knot is tightened, thereby closing the opening.

26. The knot pusher according to claim 25, further comprising a knob for holding the knot pusher, the knob being connected to a proximal end of the knot pusher.

27. The device according to claim 14, wherein the needle receiving body is rigidly coupled to the proximal portion when the needle receiving body is in a position in which the abutment contacts the stop.

* * * * *